(12) United States Patent
Flake et al.

(10) Patent No.: US 8,784,278 B2
(45) Date of Patent: Jul. 22, 2014

(54) UNDERWATER TREADMILL AND INTEGRATED JET DEVICE AND METHOD FOR SELECTIVELY CONTROLLING AN UNDERWATER TREADMILL SYSTEM

(75) Inventors: Anson Flake, Enola, PA (US);
Dominick Tucci, Middletown, PA (US);
Phillip Black, McConnellsburg, PA (US)

(73) Assignee: Hydroworx International, Inc., Middletown, PA (US)

( * ) Notice: Subject to any disclaimer, the term of this patent is extended or adjusted under 35 U.S.C. 154(b) by 696 days.

(21) Appl. No.: 13/042,506

(22) Filed: Mar. 8, 2011

(65) Prior Publication Data

US 2011/0294625 A1  Dec. 1, 2011

Related U.S. Application Data

(60) Provisional application No. 61/349,315, filed on May 28, 2010.

(51) Int. Cl.
| | | |
|---|---|---|
| A63B 22/02 | (2006.01) | |
| A63B 31/00 | (2006.01) | |
| A61H 33/00 | (2006.01) | |
| A61B 5/22 | (2006.01) | |
| A61H 33/02 | (2006.01) | |
| A63B 22/00 | (2006.01) | |
| A61B 5/11 | (2006.01) | |
| A63B 21/008 | (2006.01) | |

(52) U.S. Cl.
CPC .......... *A61H 33/027* (2013.01); *A61H 33/0087* (2013.01); *A61H 2001/1261* (2013.01); *A61B 5/222* (2013.01); *A63B 22/0023* (2013.01); *A61H 33/6026* (2013.01); *A63B 22/02* (2013.01); *A61B 5/1118* (2013.01); *A61H 2230/62* (2013.01); *A63B 21/0081* (2013.01); *A63B 2210/50* (2013.01); *A63B 21/0084* (2013.01); *A63B 2230/06* (2013.01); *A63B 2022/0264* (2013.01); *A63B 22/0235* (2013.01); *A61H 2201/1207* (2013.01); *A61H 2201/5043* (2013.01); *A61H 2230/06* (2013.01); *A63B 2220/806* (2013.01); *A63B 2225/60* (2013.01); *A63B 2207/02* (2013.01)
USPC .............................................. 482/54; 482/55

(58) Field of Classification Search
USPC ............................ 482/54–55; 119/700; 4/492
See application file for complete search history.

(56) References Cited

U.S. PATENT DOCUMENTS

| | | |
|---|---|---|
| 3,941,377 A | 3/1976 | Lie |
| 4,114,206 A | 9/1978 | Franc |
| 4,332,217 A | 6/1982 | Davis |
| 4,576,376 A | 3/1986 | Miller |
| 4,602,779 A | 7/1986 | Ogden |
| 4,712,788 A | 12/1987 | Gaudreau, Jr. |
| 4,776,581 A | 10/1988 | Shepherdson |
| 4,886,266 A | 12/1989 | Trulaske |
| 4,918,766 A | 4/1990 | Leonaggeo, Jr. |

(Continued)

*Primary Examiner* — Loan H Thanh
*Assistant Examiner* — Jennifer M Deichl
(74) *Attorney, Agent, or Firm* — McNees Wallace & Nurick LLC

(57) ABSTRACT

Disclosed are an underwater treadmill system and a method of exercising involving the underwater treadmill system. The underwater treadmill system includes a fluid-driven treadmill belt and a housing including a jet. The method includes selectively driving a fluid-driven treadmill belt by selectively providing a fluid to a treadmill drive unit and selectively expelling water through a jet positioned within a housing of the underwater treadmill system.

23 Claims, 26 Drawing Sheets

(56) References Cited

U.S. PATENT DOCUMENTS

| | | | |
|---|---|---|---|
| 4,938,469 A * | 7/1990 | Crandell | 482/54 |
| 4,944,506 A * | 7/1990 | Keller et al. | 482/54 |
| 5,108,088 A | 4/1992 | Keller et al. | |
| 5,123,641 A | 6/1992 | Abboudi et al. | |
| 5,141,479 A | 8/1992 | Vanjani et al. | |
| 5,162,029 A | 11/1992 | Gerard | |
| 5,163,885 A | 11/1992 | Wanzer et al. | |
| 5,302,162 A | 4/1994 | Pasero | |
| 5,368,532 A | 11/1994 | Farnet | |
| 5,470,293 A | 11/1995 | Schönenberger | |
| 5,518,471 A | 5/1996 | Hettinger et al. | |
| 5,558,604 A | 9/1996 | Hopkins | |
| 5,921,892 A * | 7/1999 | Easton | 482/54 |
| 6,178,570 B1 | 1/2001 | Denst et al. | |
| 6,746,375 B2 * | 6/2004 | Smith et al. | 482/54 |
| 6,857,990 B1 * | 2/2005 | Silva | 482/54 |
| 7,086,994 B2 * | 8/2006 | Turak et al. | 482/54 |
| 7,241,250 B1 | 7/2007 | French et al. | |
| 7,241,520 B2 | 7/2007 | French et al. | |
| 7,510,513 B2 | 3/2009 | De Figueiredo Silva | |
| 8,074,304 B1 * | 12/2011 | Snyder | 4/541.1 |
| 2007/0123389 A1 * | 5/2007 | Martin | 482/8 |
| 2007/0184947 A1 * | 8/2007 | Hruska | 482/111 |
| 2011/0037497 A1 | 2/2011 | Or-Bach | |
| 2012/0010052 A1 * | 1/2012 | Hof | 482/54 |

* cited by examiner

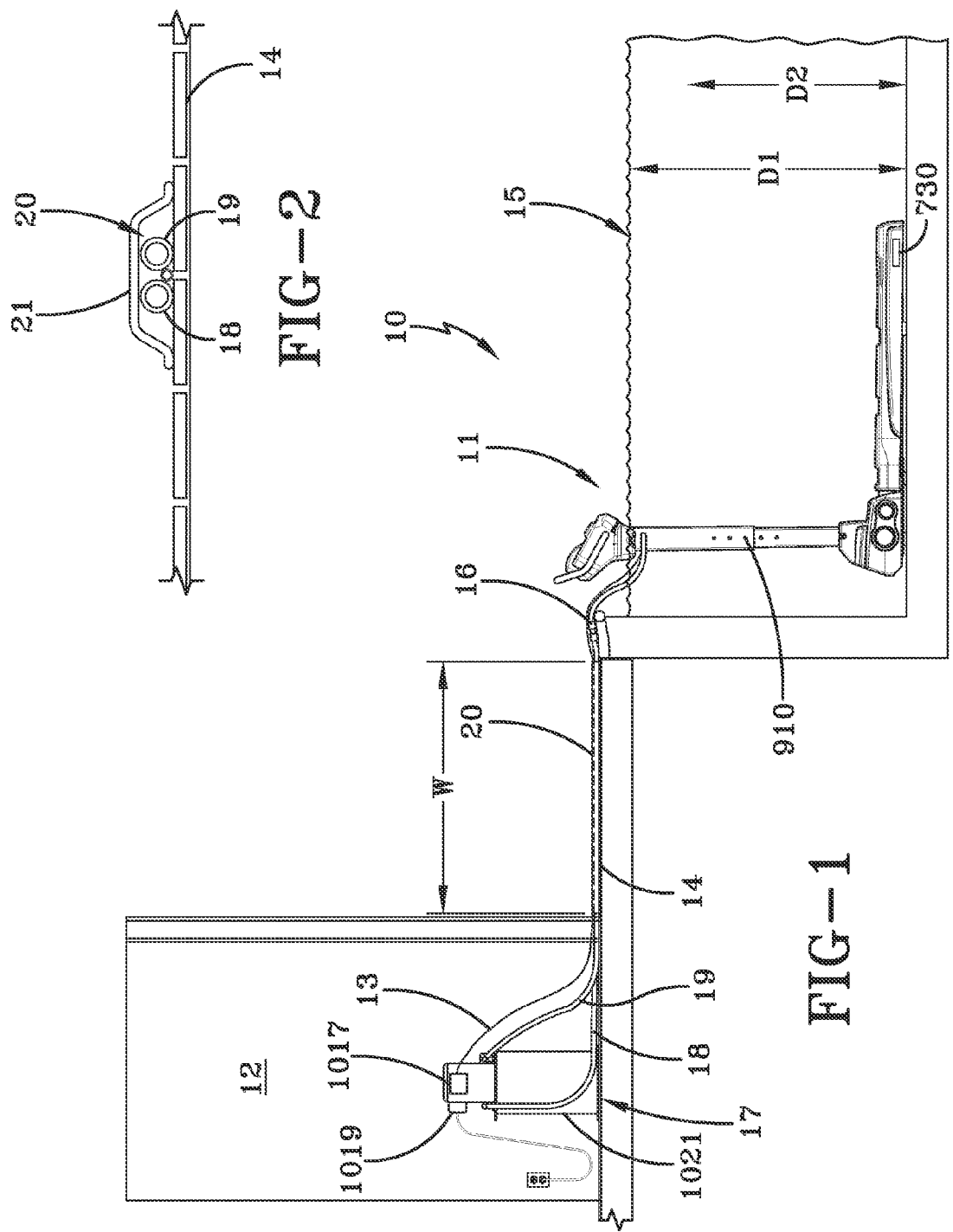

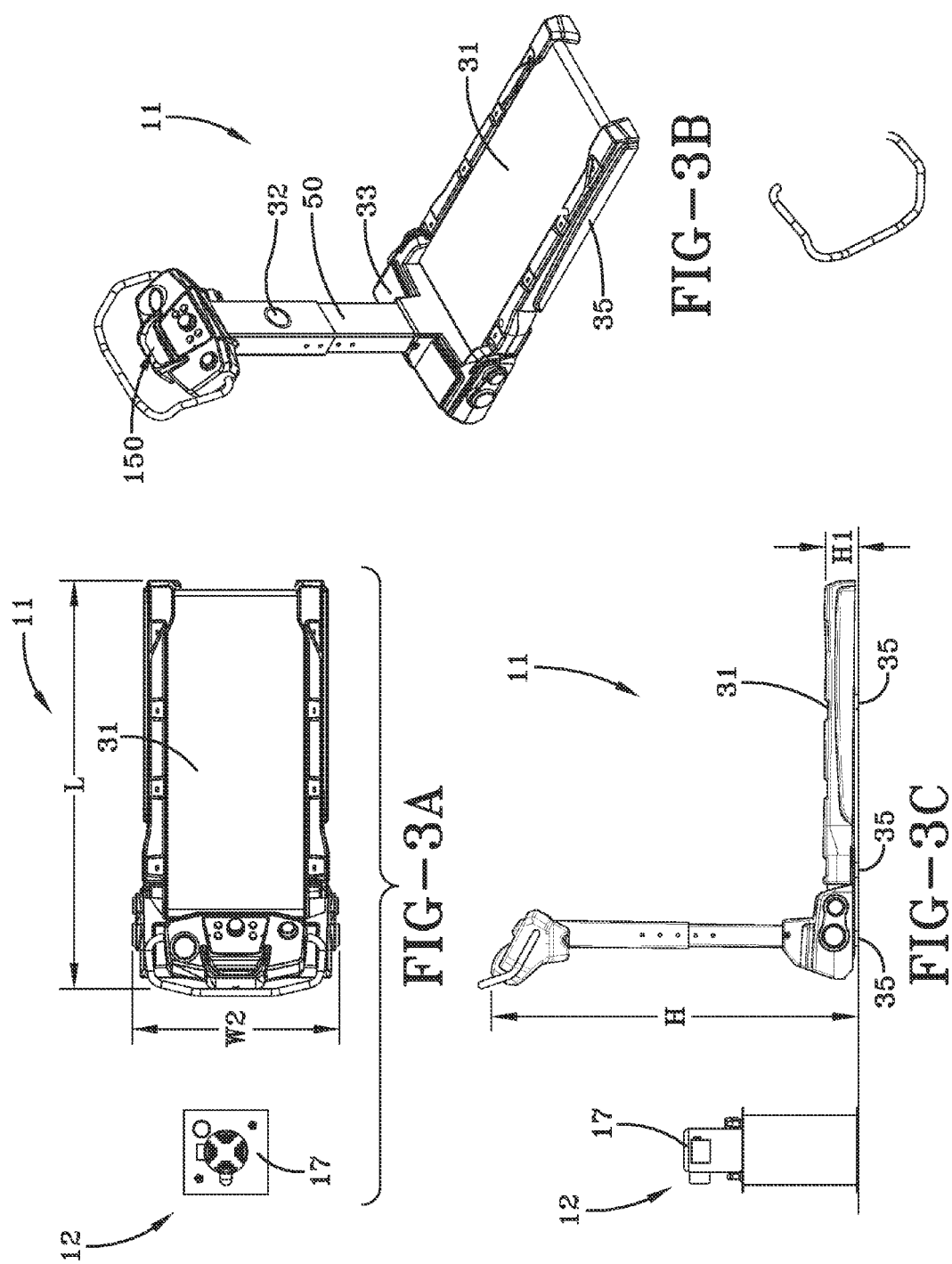

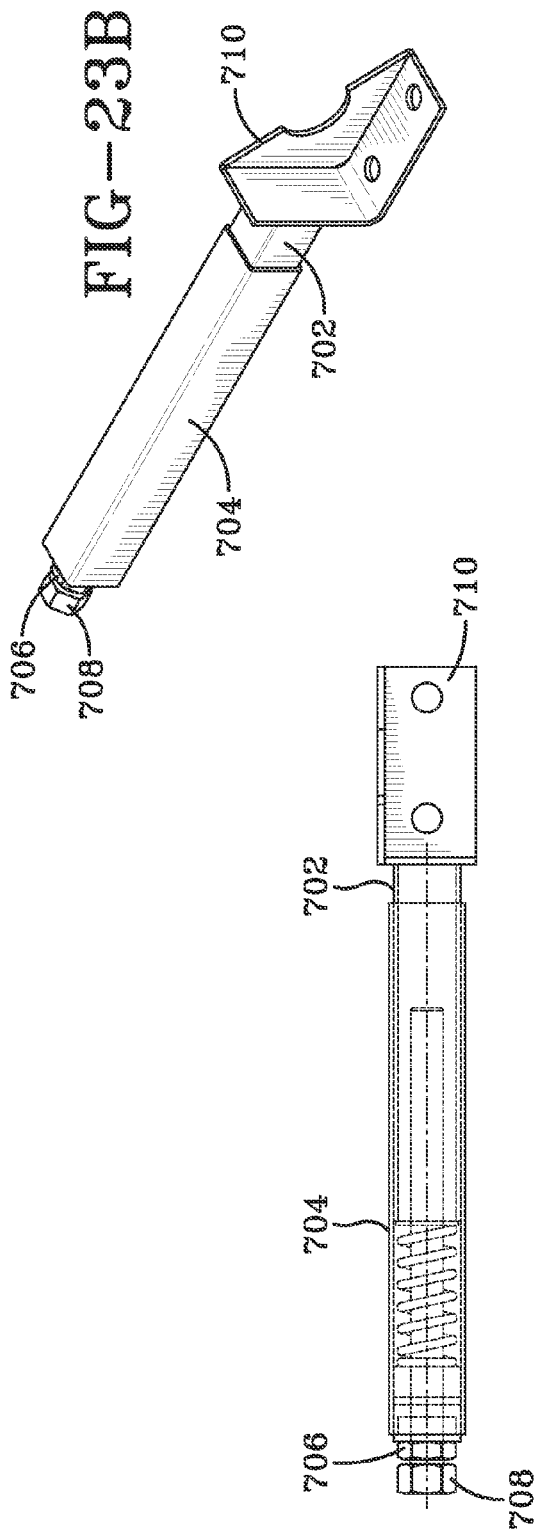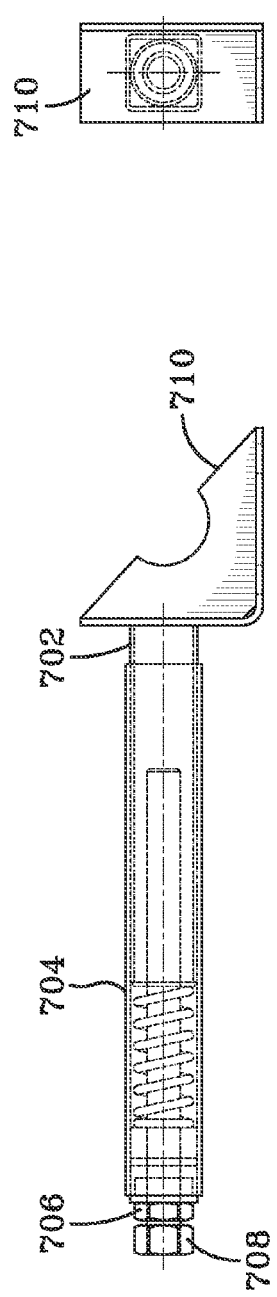

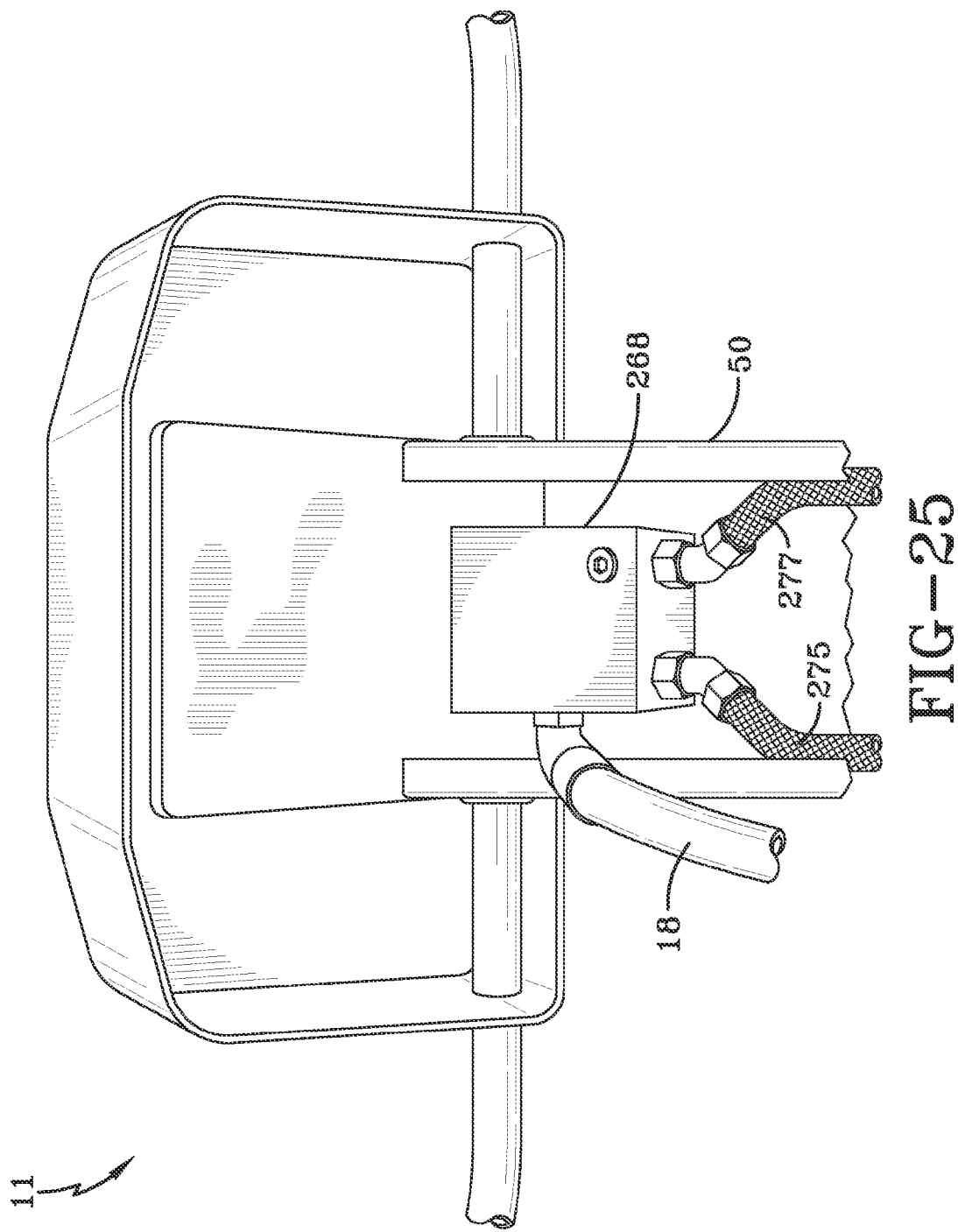

UNDERWATER TREADMILL AND INTEGRATED JET DEVICE AND METHOD FOR SELECTIVELY CONTROLLING AN UNDERWATER TREADMILL SYSTEM

FIELD OF THE INVENTION

The present invention is directed to an underwater treadmill and method for selectively controlling the underwater treadmill with the integrated jet device to accomplish exercise and physical therapy. More particularly, the present invention is directed to an underwater treadmill system that includes a treadmill and integrated jet device and exercise method involving an underwater treadmill.

BACKGROUND OF THE INVENTION

Treadmills have become increasingly popular as a form of exercise and therapy. Individuals may adjust the speed and resistance of the treadmill to suit their exercise requirements while avoiding inclement weather conditions and poor outside running surfaces. Dry treadmills, that is, treadmills that operate in a normal air atmosphere on the ground, are in widespread use and are typically found in health clubs, rehabilitation facilities, and home gyms. However, submerged or underwater treadmills are becoming more common as the benefits of running, jogging or walking on a dry treadmill can be combined with the natural resistance and buoyancy of water to reduce the strain and stress on the user's joints resulting from running or the use of a dry treadmill. Because the natural resistance of water provides reduced strain and stress, underwater treadmills also have been extremely beneficial for rehabilitation from injuries. As a result, these treadmills have found therapeutic use by senior citizens recovering from surgery or other injuries as well as by professional and amateur athletes.

However, underwater treadmills have a series of problems which are unique to the environment in which they operate. An underwater treadmill has unique power requirements, as it must have the ability to deliver the necessary power to the treadmill so that it can operate over a wide range of speeds while overcoming the resistive effects of water. Additional resistance is imposed each time the foot is planted on the treadmill surface which, when combined with the isolated motive power source, tends to cause a jerky motion in the treadmill. Further, by virtue of the buoyant effects of the water, there is a tendency for each foot plant to cause some water to squirt from beneath the moving continuous belt, thereby causing its tail end to lift upwards. Certain types of underwater treadmills that are electrically powered face the additional problem of isolating the electrical power source from the water. Finally, in swimming pools, exercise pools and the like, all metal objects associated with the treadmill must be connected to an electrically grounded pool bonding grid which tends to induce galvanic corrosion in the metal parts of the treadmill.

The use of underwater treadmills may be in a pool having specific water flow patterns or no specific water flow patterns. The water flow patterns in the pool can affect the resistance on the user, thereby affecting the overall exercise routine of therapy. These water flow patterns (or lack thereof) differ from one pool to another and differ based upon other conditions (including, but not limited to, the size and/or weight of the user, environmental conditions, the temperature of the water, the location of the treadmill within the pool and the chemicals within the water). These differences between one pool and another or between conditions at one time and another can limit the capabilities of an underwater treadmill and/or can result in inconsistent exercise or therapeutic results for the user. For example, an underwater treadmill operated in a large pool with side walls being positioned far from the treadmill may have an amount of resistance that will differ in comparison to one operated in a small pool having side walls positioned close to the treadmill, even though the treadmill settings are otherwise identical.

What is needed is an underwater treadmill system and an exercise method involving an underwater treadmill system that additionally enables permits control of resistance within the pool to be controlled and varied.

SUMMARY OF THE INVENTION

One aspect of the present disclosure includes an underwater treadmill. The underwater treadmill includes a movable, substantially continuous treadmill surface or belt, and at least one integrated air/water jet device, the jet device positioned in the treadmill housing adjacent to or in close proximity to the user. The housing comprises at least one support column. The housing also may include mechanisms and controls when the tread mill is hydraulically powered.

Another aspect of the present disclosure includes a method for selectively controlling an underwater treadmill system. The method includes selectively driving a hydraulically operated treadmill surface by selectively providing a hydraulic fluid to a treadmill drive motor from a hydraulic pump, the hydraulic pump driven by an AC motor. Water, air or a combination of water and air may be selectively expelled through at least one jet that may be positioned within or on a housing of the underwater treadmill system adjacent to or in proximity to the user. The jet includes an impeller that accelerates water within a duct to an outlet. The duct may include a nozzle at the outlet that further increases the velocity of the water as well as an air inlet to inject air into the water stream.

One advantage of the system or method is that it permits control of resistance within the pool through selective adjustment of a hydraulically driven treadmill belt as well as selective adjustment of a jet positioned within a housing of the underwater treadmill system.

Another advantage of the system or method is applicability to various pool designs while being able to reproduce exercise conditions from one pool to another. In addition, the treadmill device of the present invention can be shipped to the manufacturer or a repair facility for repair in lieu of an on-site visit by a repair technician.

Another advantage of the system or method is the mobility and positionability of the system from one pool to another or from one location within a pool to another location whereby exercise conditions can be varied in a controlled fashion.

Another advantage of the system or method is the ability to selectively adjust the air and/or water flow of a jet within a housing of the underwater treadmill system adjacent to or in proximity to the user.

Another advantage of the treadmill system is the ability to vary the type of exercises performed on the equipment of the present invention. Not only can traditional walking, running and jogging be accomplished, but also swimming and upper and lower body plyometrics can be performed. Additionally, therapeutic massage using the jet features of the present invention while rehabilitation can also be accomplished while using the exercise features of the treadmill system of the present invention.

Other features and advantages of the present invention will be apparent from the following more detailed description of the preferred embodiment, taken in conjunction with the accompanying drawings which illustrate, by way of example, the principles of the invention.

BRIEF DESCRIPTION OF THE DRAWINGS

FIG. 1 shows a schematic view of an underwater treadmill system according to an embodiment of the present disclosure.

FIG. 2 shows a sectional view of a deck proximal to a pool having an underwater treadmill system according to an embodiment the present disclosure.

FIG. 3A shows a top view of a portion of an underwater treadmill system according to an embodiment the present disclosure.

FIG. 3B shows a perspective view of a portion of an underwater treadmill system according to an embodiment the present disclosure.

FIG. 3C shows a side view of a portion of an underwater treadmill system according to an embodiment the present disclosure.

FIG. 23A shows a schematic view of a spring in an underwater treadmill portion according to an embodiment of the present disclosure.

FIG. 23B shows a schematic view of a spring in an underwater treadmill portion according to an embodiment of the present disclosure.

FIG. 23C shows a schematic view of a spring in an underwater treadmill portion according to an embodiment of the present disclosure.

FIG. 23D shows a schematic view of a spring in an underwater treadmill portion according to an embodiment of the present disclosure.

FIG. 25 shows a perspective view of a portion of an underwater treadmill system according to an embodiment of the present disclosure.

DETAILED DESCRIPTION OF THE INVENTION

Figure 4:
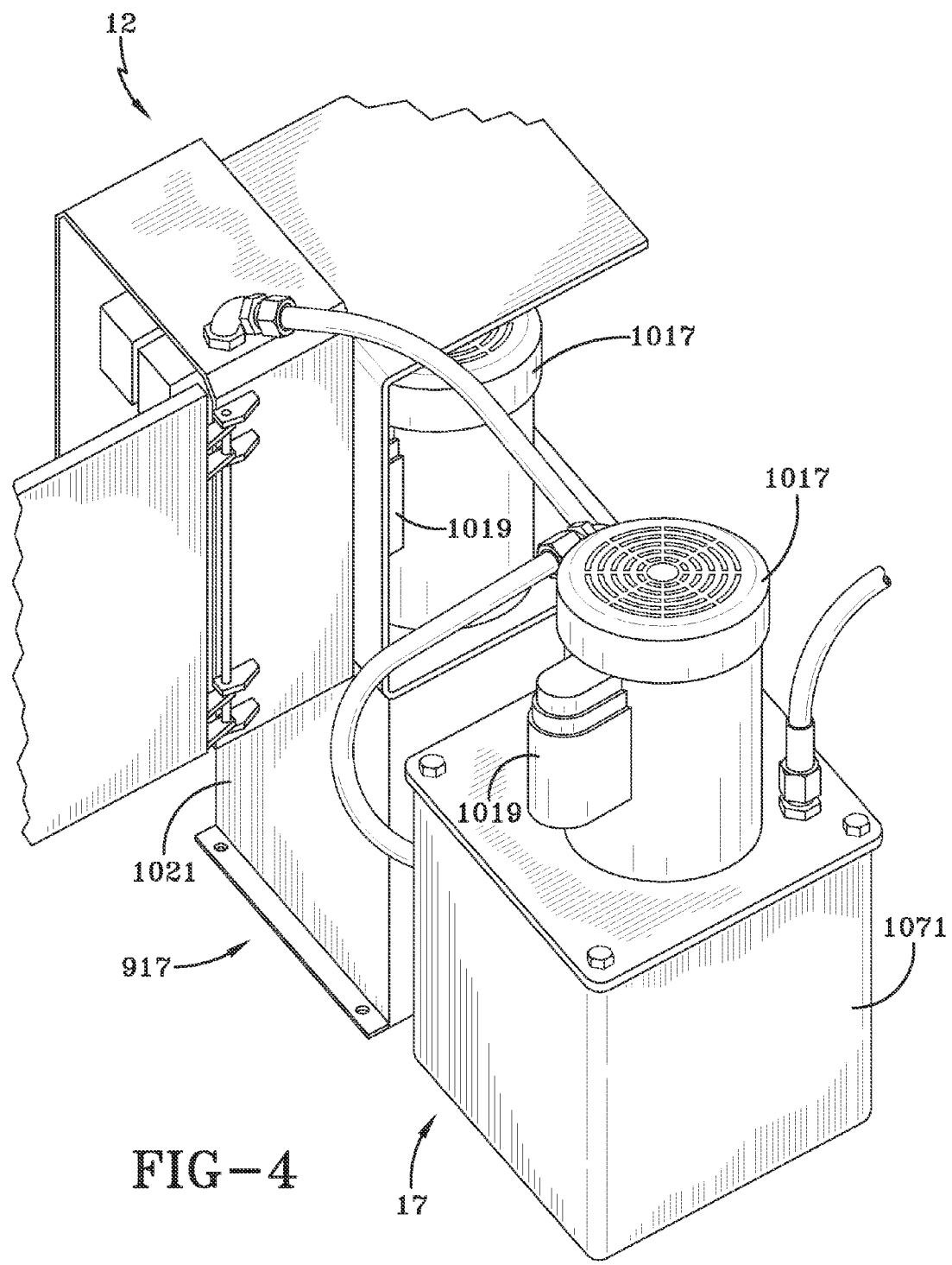
FIG. 4 shows a perspective view of a pump of an underwater treadmill system according to an embodiment of the present disclosure.

An underwater treadmill having an integrated jet device and a method of using such an underwater treadmill system is set forth. Embodiments of the system and method provide selectively controllable water flow, treadmill speed and treadmill inclination, for use in various pool designs. Selectively controllable air injection into the water flow may also be provided. The system is mobile, and is positionable within a pool, while allowing the user to selectively adjust water flow in conjunction with the adjustment of a treadmill. Although set forth as hydraulically operated, the treadmill portion of the system may be powered by any power source, including self-propulsion by the user.

FIG. 1 shows a schematic view of an underwater treadmill system 10 according to the present invention. In a preferred embodiment, the system 10 includes a submergible treadmill portion 11, a non-submergible portion 12, preferably located adjacent to the pool 15 or body of water, and optionally at least one conduit 20 for hoses and wires, such as hydraulic lines, connecting submergible treadmill portion 11 to non-submergible portion 12. Conduit 20 can include a plurality of wires 13 and/or hydraulic hoses for controlling the submergible treadmill portion 11 (for example, start/stop control wires) connecting non-submergible portion 12 to submergible treadmill portion 11. Optional conduit 20 can extend across deck 14 (or other suitable surface) proximal to a pool 15 and can be secured by one or more fittings 16 (for example, fittings for connecting hydraulic hoses of submergible treadmill portion 11 to hoses from non-submergible portion 12, fittings for securing conduit 20 to deck 14, and/or other suitable fittings). Deck 14 can be any suitable and convenient width. For example, deck 14 may have a width of about 5 feet and the hoses or control wires may be provided in sufficient length to span deck 14.

FIG. 1 also shows that submergible treadmill portion 11 can be submerged within a depth range, as indicated by D1 and D2. For example, submergible treadmill portion 11 can be submerged at a first depth D1, at a second depth D2, the first depth D1 being greater than the second depth D2 or at any depth between D1 and D2. In one embodiment, the first depth D1 may be about 4.5 feet and the second depth D2 may be about 3.66 feet. The depth may be determined by either the desired workout regime or rehabilitation program. Submergible treadmill portion 11 can have a predetermined weight sufficient to overcome its own buoyancy and capable of maintaining submergible treadmill portion 11 on the bottom of pool 15. A typical weight for submergible treadmill portion 11 is in the range from about 150 pounds to about 400 pounds so that it can be removed from the pool. Submergible treadmill portion 11 may also include a mechanism such as rollers or wheels to facilitate its movement within the pool or after removal from the pool, the rollers or wheels being inactivated when submergible treadmill portion 11 is in use. Non-submergible portion 12 includes at least a supply line 18 and/or a return line 19 for providing a hydraulic fluid to submergible treadmill portion 12, and/or other suitable components.

FIG. 2 shows a sectional view of deck 14 with conduit 20 positioned on deck 14. More than one conduit can be included and conduit 20 may be positioned under deck 14. Conduit 20 can be a tube of sufficient size to completely or partially enclose hydraulic supply line 18, hydraulic return line 19, and/or the wires 13 (see FIG. 1) for adjusting the submergible treadmill portion 11. Deck 14 can be provided with a false bottom and conduit 20 can be run under the false bottom to the pool to minimize hazards such as tripping due to inattention. Conduit 20 may be run through a wall in the false bottom of deck 14 or through a wall of the swimming pool to provide a communications route into the swimming pool to the submerged treadmill. Conduit 20 further may be at least partially secured under the false bottom. In one embodiment, conduit 20 can be secured to deck 14 by a cover 21. Cover 21 can be a water-resistant or water-proof material with an adhesive (or other suitable fastening mechanism such as Velcro or bolting) securing cover 21 to deck 14. In one embodiment, cover 21 can include a design and/or color to blend in with the deck 14. In another embodiment, cover 21 can include a design and/or color to contrast with that of the deck 14 (for example, identifying the conduit as a tripping hazard). Cover 21 may simply be removable decking material.

Figure 9:
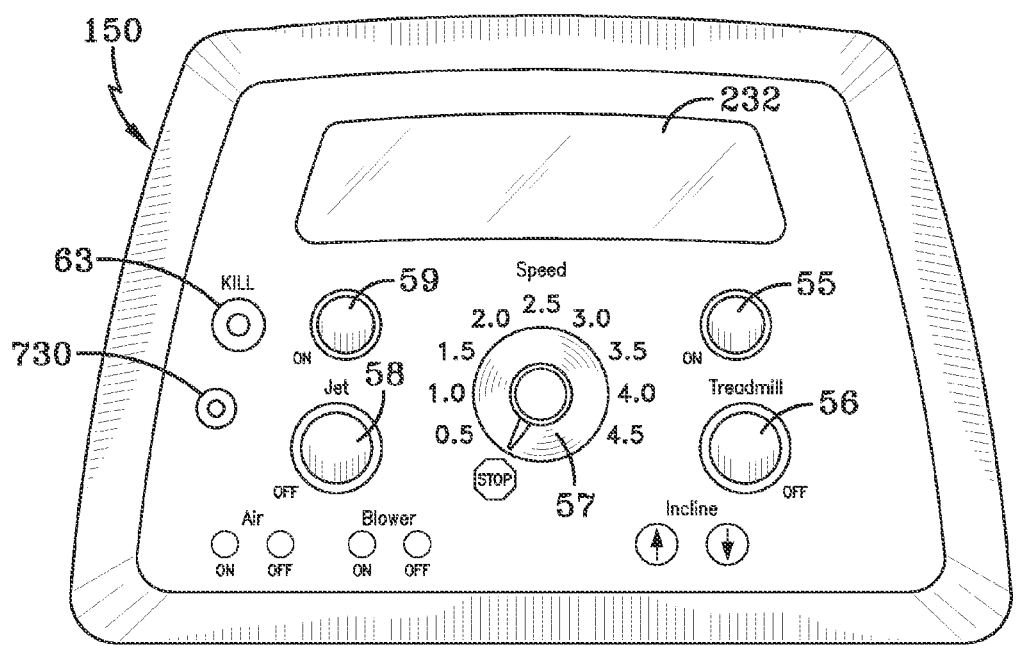
FIG. 9 shows a top view of a console of an underwater treadmill system according to an embodiment of the present disclosure.
Figure 22:
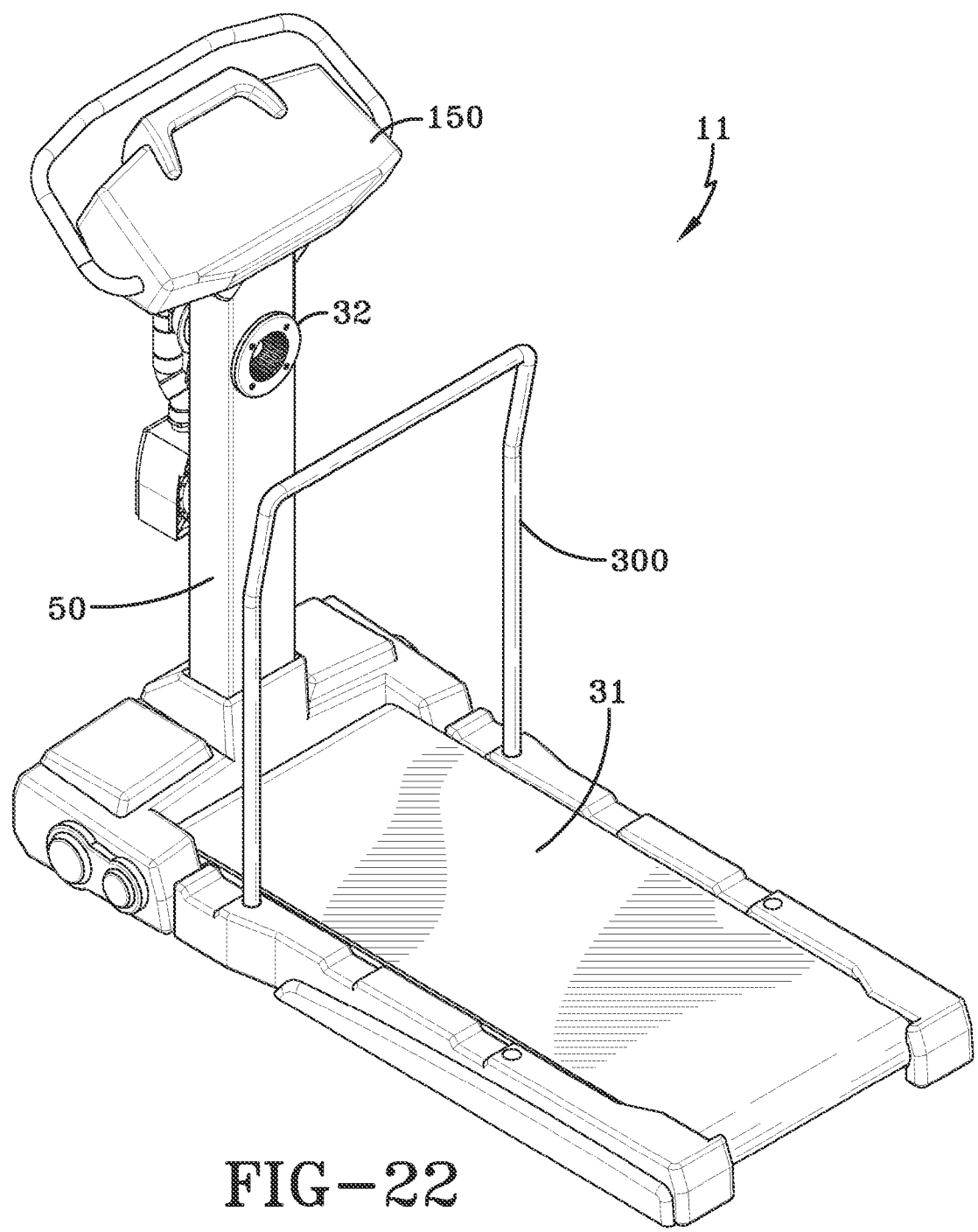
FIG. 22 shows a perspective view of a portion of an underwater treadmill system having a cross rail according to an embodiment of the present disclosure.
Figures 24A, 24B, 24C, 24D:
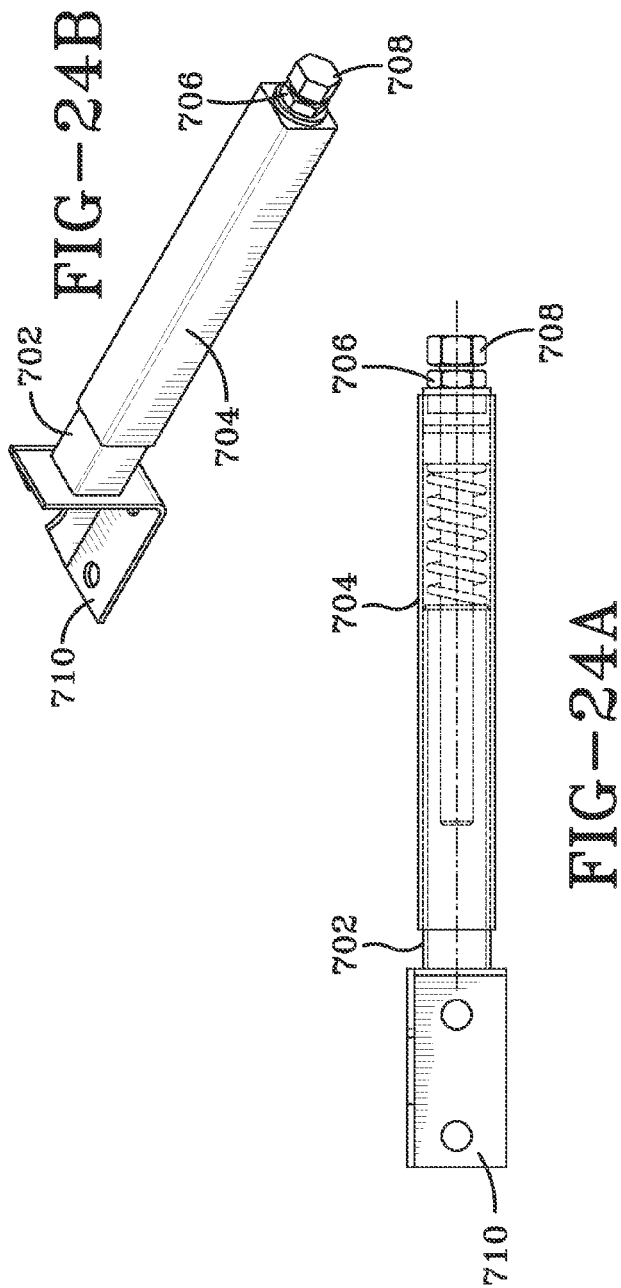
FIG. 24A shows a schematic view of a spring in an underwater treadmill portion according to an embodiment of the present disclosure.
FIG. 24B shows a schematic view of a spring in an underwater treadmill portion according to an embodiment of the present disclosure.
FIG. 24C shows a schematic view of a spring in an underwater treadmill portion according to an embodiment of the present disclosure.
FIG. 24D shows a schematic view of a spring in an underwater treadmill portion according to an embodiment of the present disclosure.

Referring further to FIGS. 3A, 3C and 4, two hydraulic drive tanks are housed in non-submergible portion 12 separate from the submergible treadmill portion 11. Each hydraulic tank drive 17, 917 includes a hydraulic pump 1017, an electric motor 1019 to power the pump, and a fluid reservoir 1021 to provide for fluctuations of fluid within the hydraulic drive system. As shown in FIG. 1, the non-submergible portion 12 can be housed within an enclosure preventing or limiting the components of the non-submergible portion 12 from being exposed to water, chemicals, and/or people. The electric motors 1019 used to drive hydraulic pumps 1017 are AC motors that typically may vary from 1 horsepower (HP) to 3 HP, depending upon the power needed to drive hydraulic pumps 1017, although electric motors having greater or less capacity may be used. Hydraulic pumps rated from 17-21 cc (cubic centimeters) may also be used, although pumps with greater or less capability may be employed. Typically, the pump size is matched to the capacity of the electric motor. The control system, which will be discussed below, permits AC electric motor 1019 and hydraulic pump 1017 to operate at a single speed which simplifies the design, although variable speed electric motors and multispeed pumps may be utilized. Hydraulic fluid from pump 1017 in first hydraulic tank drive 17 is provided to a proportional valve 268, see FIGS. 10 and 25, located within or on housing 50, FIG. 22. Referring to FIG. 9, knob, which is in fact a control actuator 57 controls the flow of fluid through proportional valve 268, which in turn controls the speed of the treadmill track. When control activator 57 is turned fully counterclockwise, as shown in FIG. 9, all of the flow from pump 1017 of first hydraulic tank drive 17 through supply line 18 is diverted by proportional valve 268 through return hose 19 to pump 1017 in first hydraulic tank drive 17 so that no fluid is provided to power treadmill drive motor 220. When control activator 57 is turned fully clockwise, a maximum amount of fluid flow from pump 1017 of first hydraulic tank drive 17 is supplied by supply line 18 and passes through proportional valve 268 to motor supply line 275, FIG. 5, to drive power treadmill drive motor 220 at its maximum speed, after which the fluid is returned through motor return line 277, back to return line 19 and to pump 1017 in first hydraulic tank drive 17. At any intermediate position, the fluid flow being proportional to the position of control activator 57, some fluid flow passes through proportional valve 268 to motor supply line 275, and some fluid flow is diverted through proportional valve 268 to return line (hose) 19. The speed at which the treadmill operates is proportional to the fluid flowing to motor supply line 275 (or alternatively stated to the fluid diverted to return line 19). Line 277 reconnects to line 19 at some point, preferably within housing 50 to return the hydraulic fluid to pump 1017 in first hydraulic tank 17. Fluid is urged through the supply line 18, proportional valve 268 and then through motor supply line 275 to treadmill drive motor 220 (see FIG. 5) to drive a fluid-driven belt 31 of the submergible treadmill portion 11. Motor 220 drives a shaft 1023 which rotates the gear and pulley system 291, moving the continuous treadmill surface. Some, none or all of the hydraulic fluid may be diverted through the proportional valve 268 to line 19. However, all of the hydraulic fluid is returned to pump in first hydraulic tank drive 17 by return line 19 once line 277 reconnects to line 19, preferably within housing 50. In this manner, the treadmill speed is controlled hydraulically. Because the hydraulic controls regulate flow through proportional valve 268, hydraulic pump 1017 only need operate at a single speed, and the electric motor 1019 only need drive the hydraulic pump at a single speed. However, more expensive multispeed pumps and electric motors may be used to control fluid flow if desired.

The treadmill surface may be any continuous surface such as an endless belt, a plurality of connected slats that form a loop, a rotating tread, etc. Thus, as used herein, any of the forms of continuous loop surface that can be driven may be used on the treadmill apparatus of the present invention and are interchangeable.

Referring to FIG. 3B, submergible treadmill portion 11 includes belt 31, at least one jet 32, and a housing 50. Belt 31 extends around a portion of the submergible treadmill portion 11 and is configured to be used by a user for walking or to perform other exercises as belt 31 continuously is driven by the drive motor 220 (see FIG. 5). Jet 32 may also be activated.

In one embodiment of the invention depicted in FIG. 3, submergible treadmill portion 11 that includes a belt 31 and at least one jet 32 mounted in or on housing 50 may be driven electrically using low voltage DC current, instead of hydraulically, if proper grounding is provided to the system.

Referring again to FIG. 5, Belt 31 extends around a drive roller 801 and an idler roller 803. Drive roller 801 preferably is a stainless steel cylinder of constant diameter that extends substantially across the width of W2 of the unit. Drive roller 801 is driven by a standard gear and pulley system 291 visible on the left side of FIG. 5, which in turn is driven by hydraulically driven drive motor 220. Idler roller 803 also preferably is a stainless steel cylinder that utilizes bearings. The bearings may be any conventional roller bearings, ball bearings, pen bearings and the like that are corrosion resistant. Preferably the bearings are made of stainless steel.

Treadmill drive unit 220 motor can be concealed and/or sealed by a base 33 (see FIG. 3B). The base 33 can be a plastic base. Referring to FIG. 3C, in one embodiment, one or more levelers 35 can maintain the belt 31 in a level orientation. Likewise, leveler(s) 35 can be used to increase or decrease the slope of belt 31. The raising or lowering of leveler(s) 35 can provide a slope or inclination for the user.

Figure 5:
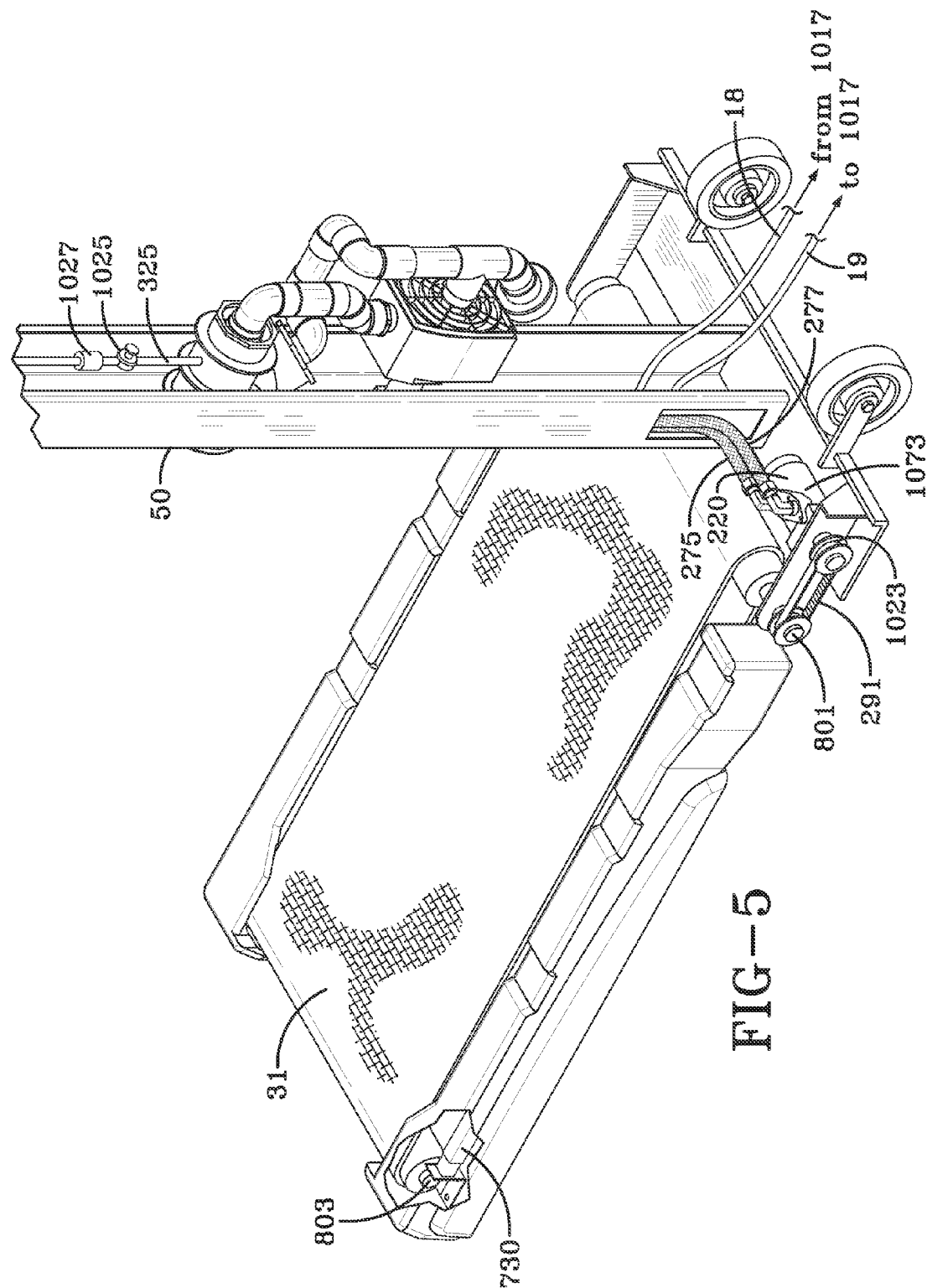
FIG. 5 shows a perspective view of a treadmill drive unit of an underwater treadmill system according to an embodiment of the present disclosure.

Referring to FIG. 5, drive motor 220 can be any suitable hydraulic drive motor capable of operation underwater and capable of being driven by a closed loop system for the hydraulic fluid that is isolated from the water in the pool. Hydraulic fluid may be any hydraulic fluid, since the fluid is isolated from the pool water, but a biodegradable hydraulic fluid is preferred in the event of an unanticipated leak. In one embodiment, treadmill drive motor 220 is driven with hydraulic fluid provided by supply line 18 that may branch from conduit 20. In one embodiment, the hydraulic fluid supplied by supply line 18 is provided from the hydraulic pump 1017 in first hydraulic tank 17 at a substantially constant flow rate. In the preferred embodiment, treadmill drive motor 220 is capable of driving belt 31 at multiple speeds by controlling flow through proportional valve 268 with actuator 57, the hydraulic fluid being recycled through the return line 19 to pump 1017 in first hydraulic tank 17.

Figure 6:
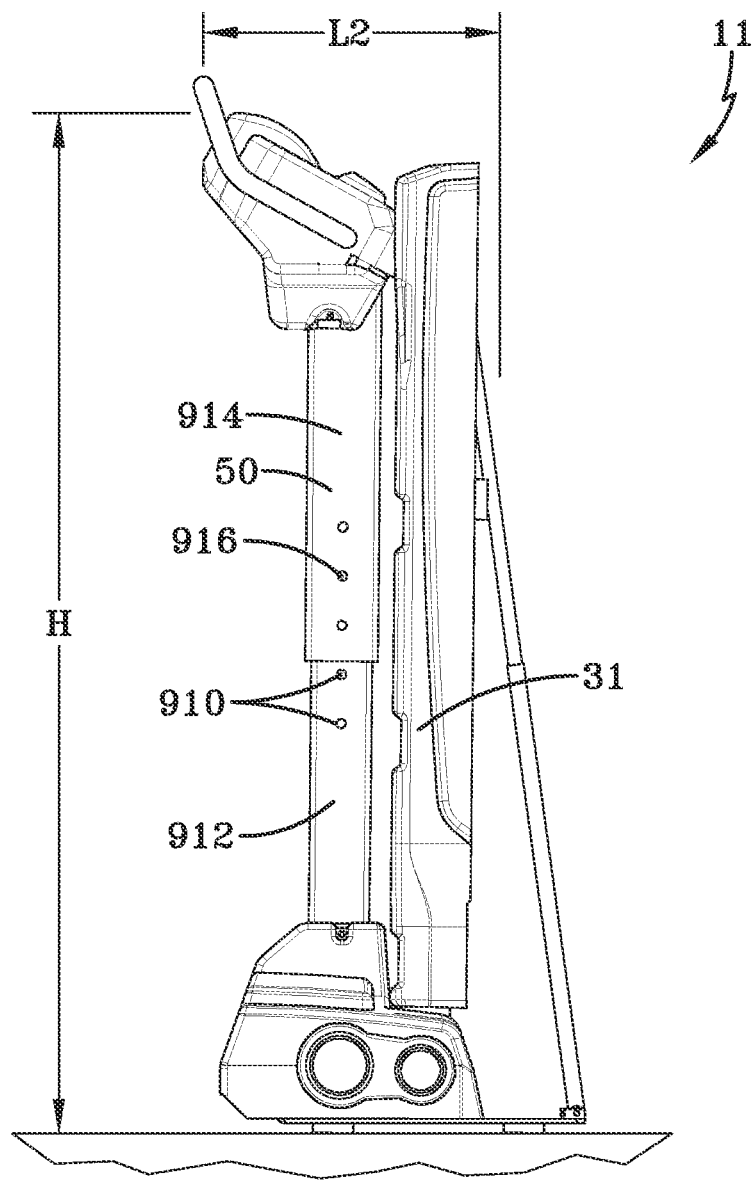
FIG. 6 shows a side view of a portion of an underwater treadmill system having a collapsed body according to an embodiment of the present disclosure.

Referring again to FIGS. 3A and 3C, submergible treadmill portion 11 is sized to preselected length L, width W2, and height H. Submergible treadmill portion 11 includes treadmill belt 31 extending a majority of the length L of the submergible treadmill portion 11 and looping around desire roller 801 and idler roller 803 to form a continuous treadmill belt. Submergible treadmill portion 11 includes jet 32 that is positioned at a predetermined position along the height H of the submergible treadmill portion 11 within housing 50. Jet 32 is positioned so that water from jet 32 can be directed at any desired body part of a user on treadmill belt 31 or at the surface of water in pool 15. The predetermined position of jet 32 preferably can be at just above about half of the height H of the submergible treadmill portion 11. As shown in FIG. 6, housing 50 with folded treadmill 31 has a preselected length L2 which is a fraction of overall length L.

As shown in FIG. 6, submergible treadmill portion 11 can be collapsed to an upright position. In the upright position, submergible treadmill portion 11 not only saves space, but also protects treadmill belt 31 and/or jet 32 by positioning treadmill belt 31 against or near jet 32. This positioning can prevent damage of treadmill belt 31 and/or jet 32 while submergible treadmill portion 11 is in storage, being moved, and/or not in use. When in the upright position, the treadmill is easier to move. As shown in FIG. 6, in one embodiment, when submergible treadmill portion 11 is upright preferably no portion extends beyond the height H of submergible treadmill portion 11. Additionally, when submergible treadmill portion 11 is upright, preferably no portion extends beyond the length L2 of housing 50. In another embodiment, upright submergible treadmill portion 11 includes features for storing or collapsing the submergible treadmill portion 11. For example, submergible treadmill portion 11 can include channels for storing rails (further described below with reference to FIGS. 12, 20, and 22). A console 150 that conveniently includes the controls for operating the treadmill unit, including treadmill belt 31 and jet 32, may be conveniently provided integral with housing 50 or may be removably mounted on top of housing 50.

Both housing 50 and console 150 comprise a corrosion resistant material. Housing 50 and/or console 150 can also be adjusted in the vertical direction. Preferably housing 50 is in tubular form having two sections, 912, 914 that telescope with respect to one another. Referring to FIG. 1 and FIG. 6, a plurality of apertures 910 extend through tubular sections 912, 914, and a removable locking device 916 such as a pin, locks the sections with respect to each other. The console height can be adjusted along H to accommodate the heights of different users or different water levels by removing locking device 916, adjusting one tubular section 912 with respect to the other tubular section 914, aligning apertures 910 in the tubular sections with respect to one another and reinserting locking device 916. Alternatively only section 912 requires apertures. Once locking device 916 is inserted in aperture 910, section 914 can be lowered onto locking device 916 which supports section 914.

Figure 7:
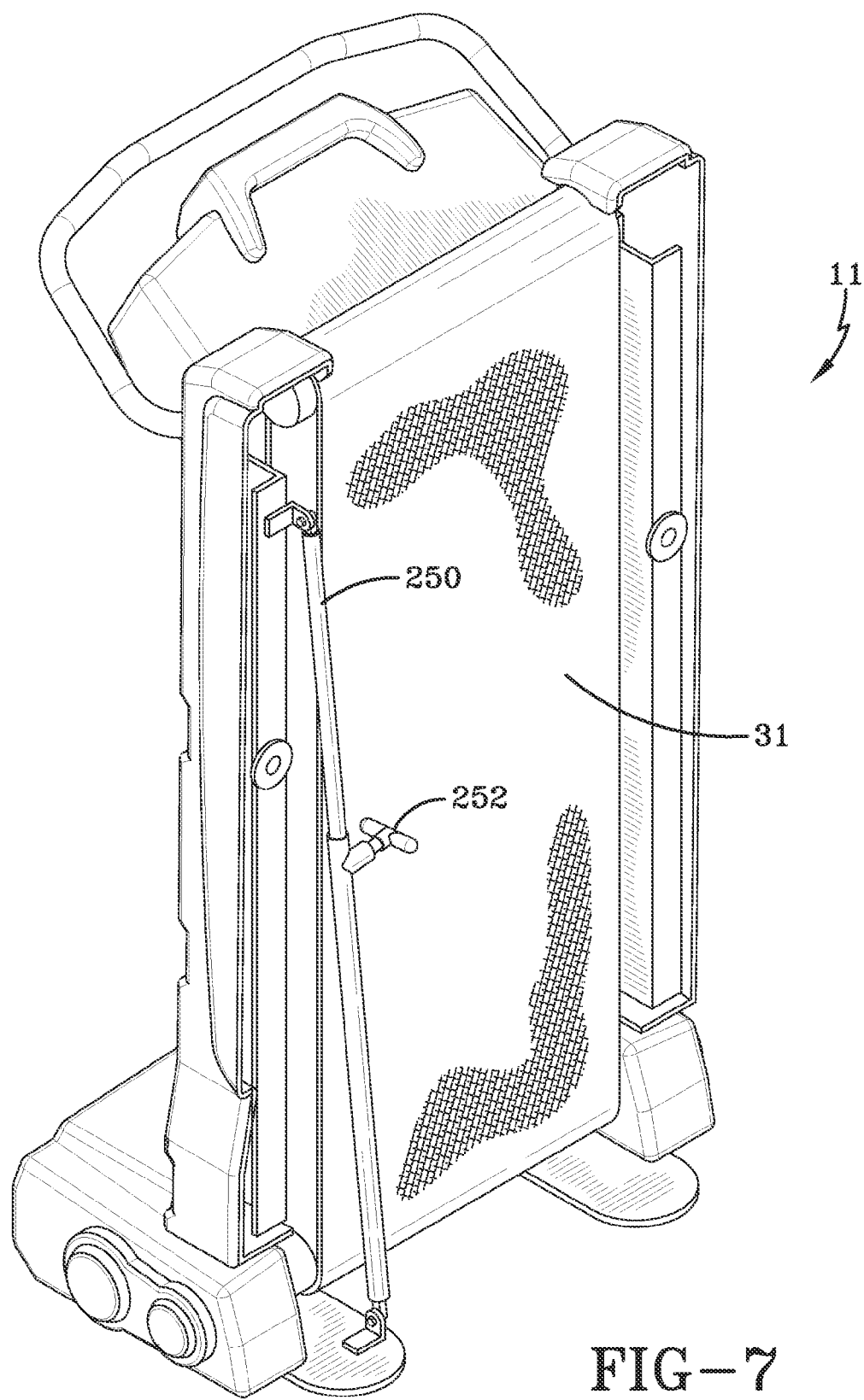
FIG. 7 shows a side view of a portion of an underwater treadmill system collapsed according to an embodiment of the present disclosure.

Submergible treadmill portion 11 may include a securing feature. The securing feature selectively locks the submergible treadmill in the upright position. Referring to FIG. 7, in one embodiment, the securing feature includes a pivotable member 250 having an aperture (not visible in FIG. 7). Pivotable member 250 is a tube in a preferred embodiment, movable by manipulating a spring-loaded handle 252, thereby releasing handle 252 from the aperture (not visible in FIG. 7). When in the collapsed/upright position, handle 252 is released from member 250 by pulling on handle 252, allowing the treadmill to be lowered. Upon being raised into the upright position, submergible treadmill portion 11 is selectively locked in an upright position by handle 252. Handle 252 rides along the outer surface of member 250, which pivots as the treadmill is raised, until spring-loaded handle is urged into the aperture on tube 250, thereby locking it in place. If desired, handle 252 may be inserted through a through-hole in pivotable member 250 and into an aperture in adjacent structure on the treadmill to prevent movement of member 250.

Figure 8:
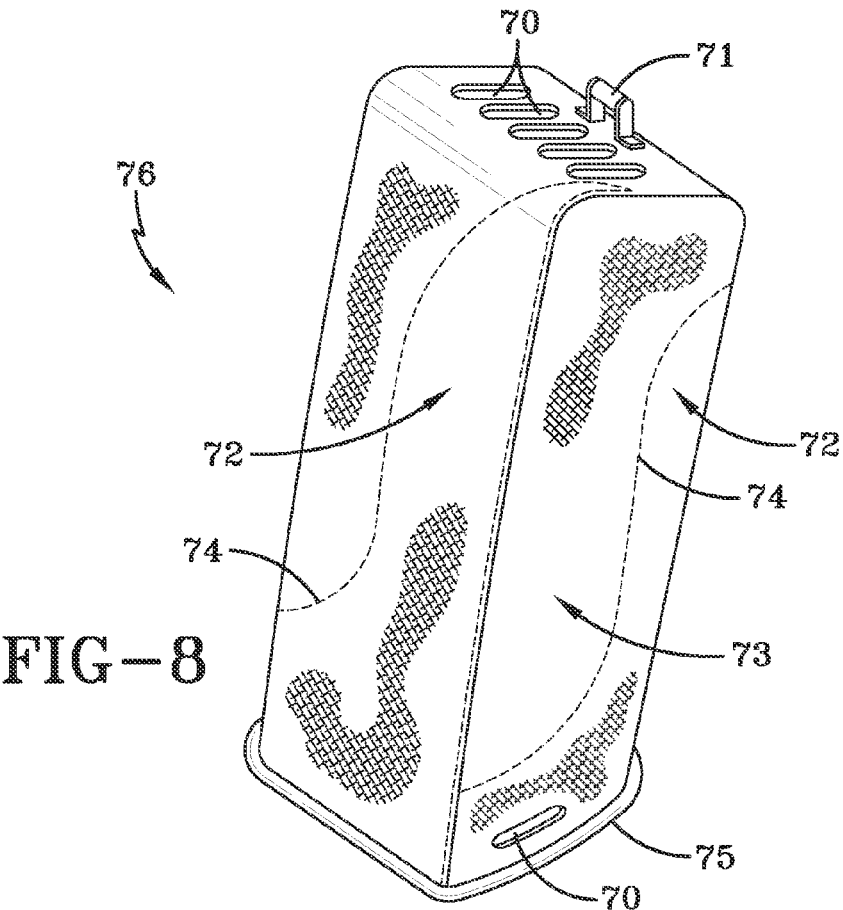
FIG. 8 shows a perspective view of a case for a collapsed submergible portion of an underwater treadmill system according to an embodiment of the present disclosure.

Referring to FIG. 8, submergible treadmill portion 11 can be configured to be enclosed by a cover or case 76 when submergible treadmill portion 11 is in the upright position. Cover or case 76 can include features for assisting in positioning it over upright submergible treadmill portion 11. For example, cover or case 76 can include a handle 71 for positioning and removing cover or case 76. Slots 70 allow air to be expelled from case 76 when case 76 is being positioned over submergible treadmill portion 11 with a downward motion into the water and on submergible treadmill portion 11 within pool 15. A weighted bottom portion 75 (for example, a sewn-in tube filled with sand and permanently secured) prevents the cover or case 76 from floating. Other suitable features (for example, being designed to fit in only one orientation, being designed to fit in multiple orientations, having alignment features, having latches, etc.) may be included in the design of cover or case 76.

Cover or case 76 may include any suitable waterproof and/or water-resistant material. Cover or case 76 may be designed to avoid fading or degradation from chemicals in the pool 15. Cover or case 76 may include any suitable aesthetic or design features. For example, cover or case 76 can include logos or colors of a desired sports team. In the embodiment shown in FIG. 8, case 76 includes three separate design regions: a first region 72, a second region 73, and stitched seams 74 bordering first region 72 and second region 73, although any other series of patterns may be employed.

FIG. 9 represents one layout for console 150, although other layouts may be used. Console 150 may be integral with housing 50, positioned on top of housing 50 or may be separate from housing 50. Console 150 conveniently lays out the controls for operation of the treadmill, jet 32, auxiliary equipment associated with the treadmill, as well as monitoring apparatus, in an ergonomic, readily accessible manner. Console 150 may include features for monitoring and/or adjusting operation of submergible treadmill portion 11. For example, console 150 may include features for monitoring and/or adjusting operation of the belt 31, such as belt speed or belt inclination and/or operation of jet 32. Console 150 may include a timer in display window 232 for monitoring the duration of exercise routines and/or for monitoring the time of operation, a heart rate monitor for monitoring the heart rate or pulse of a user or other functions. The speed of treadmill belt 31 also may be displayed in display window 232. Console 150 may include a start mechanism 55 for engaging the electric motor(s) associated with pumps 17 and 917 to move belt 31 and activate jet 32. Console 150 may also include a stop mechanism 56 for the treadmill, a stop mechanism 58 for jet 32 and a kill switch 63 to immediately stop all functions associated with the operation of the treadmill, such as by stopping electric motors associated with operation of the treadmill or by cutting electric power to the treadmill. In one embodiment, the start mechanism and the stop mechanism may be activated by depressing the same button (for example, the start mechanism is activated by pressing the button while the belt 31 is stationary and the stop mechanism is activated by pressing the same button while the belt 31 is moving). Console 150 includes an actuator 57 for selectively adjusting a velocity of the belt 31. As previously discussed, actuator 57 controls the flow of fluid through proportional valve 268, which controls the speed of treadmill belt 31.

Console 150 may include a separate jet stop mechanism 58 and jet start mechanism 59 for actuating the electric motor 1019 for pump 317,1017 which activates jet 32. In one embodiment, a control 230 for modulating an amount of water being driven through jet 32 may be included as a button, switch, lever or the like on console 150 to control an optional proportional valve 278 which controls the flow of water to jet 32. Adjusting device 230 used in conjunction with optional proportional valve 278 can permit selective adjustment that can be repeated or varied to form a massaging effect directed at a user on the treadmill. Alternatively, or in addition to adjusting device 230 and optional proportional valve 278, an adjusting device 130 which acts as a flow control nozzle may be integral with jet 32 and may be controlled by twisting or rotating the adjusting device 130 to control the proportion of air and water flowing through the jet. Adjusting device 130 may include several functions. It acts as a nozzle component of jet 32 to channel water flow toward a user. It also may be twisted to adjust the flow of fluid through the opening, to the point of substantially throttling the flow of fluid open or closed through its opening. Adjusting device 130 can be pivoted through 360° to direct the flow of fluid up or down or from side to side as desired by the user. Thus, adjusting device 130 acts as a nozzle for the flow of fluid through jet 32, and for throttling the flow of fluid from jet 32. It also can be used to adjust the direction of the flow of fluid from jet 32. As used herein, it may be referred to interchangeably as an adjustment feature or as a nozzle, as it simultaneously may perform these functions.

In certain embodiments, pump 1017 powering jet 32 can allow jet 32 to provide sufficient force to create a current in the body of water to permit the user to exercise by swimming against the current. The force of fluid produced by jet 32 and the direction of the fluid from jet 32 can be varied so that a current is directed toward the water surface and the velocity of the current equals the swimming speed of the user, consistent with the swimming activity of the user. The current has sufficient force to counteract the activity of the user. The current provided is self-correcting, which is to say, if the current is too strong, it will push the swimmer away from jet 32. However, the force generated by the current dissipates with distance from jet 32, so that at some point along the surface the velocity of the current will equal the speed of the swimmer. Although described herein as jet 32, any other device integral to submergible treadmill portion 11 that provides a current the permits a swimming activity or massaging function with a stream of fluid and emanating from submergible underwater treadmill portion 11, such as from housing 50, may be used in place of or as a supplement to jet 32.

As shown in FIG. 9, console 150 includes optional controls 64, 65 for opening or closing optional air valve 1025 and for activating optional blower motor 1027 when air valve 1025 is open. The speed of blower motor 1027, when it is a multiple speed motor, may be controlled my multiple pushes on on-button 65. The status of these functions may be displayed in display window 272. The slope or incline of belt 31 may be controlled by incline controls 66 which raise or lower the slope of belt 31. The slope of belt 31 may be displayed in display window 232.

Figure 26:
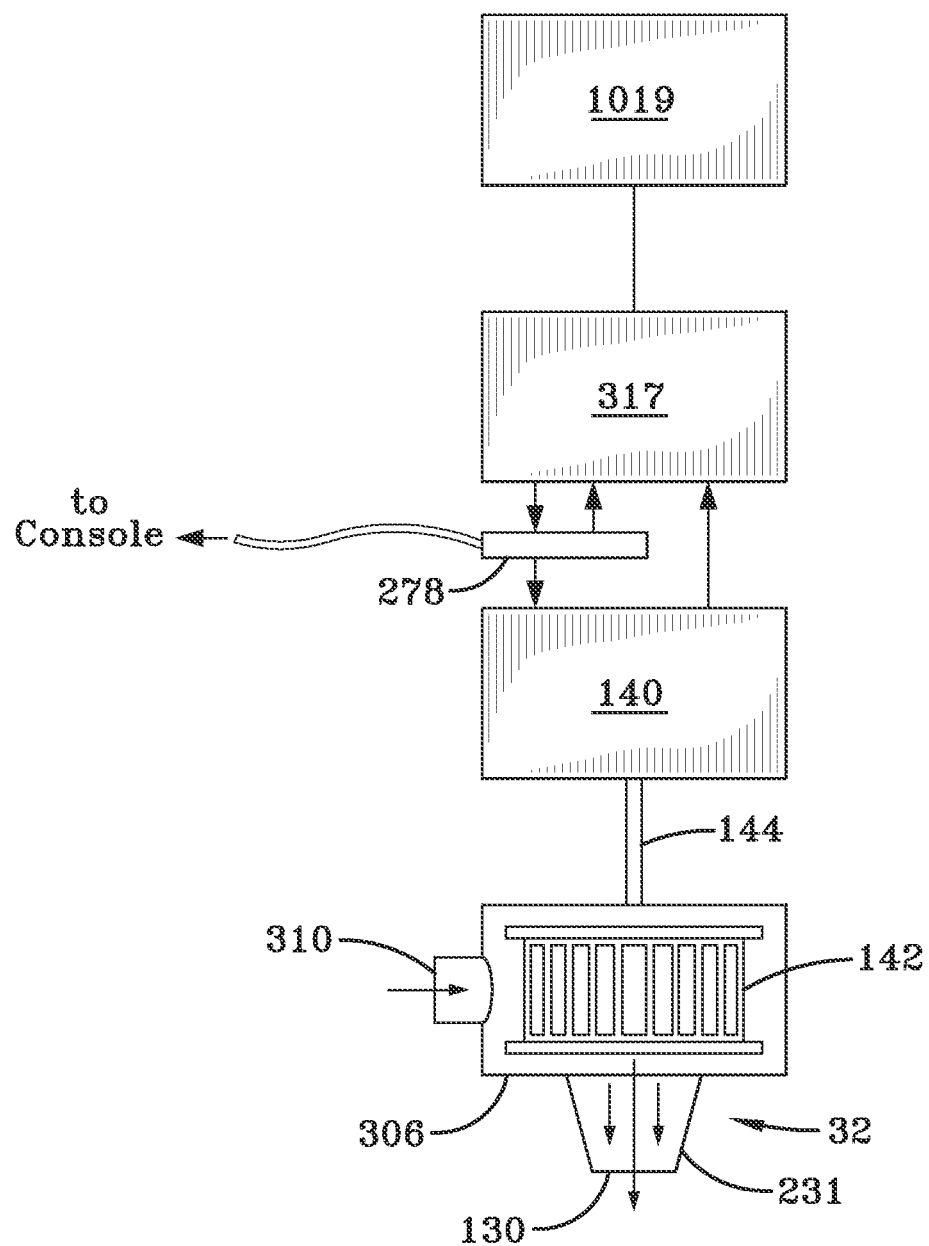
FIG. 26 schematically depicts the arrangement of an electric motor in series with a hydraulic pump and a hydraulic motor to drive an impeller to provide a stream of fluid to a nozzle.

Operation of jet 32 is further described by reference to FIGS. 26 and 27. A hydraulically operated fluid motor 140 operates in a closed hydraulic circuit. The closed hydraulic circuit may be a single hydraulic tank drive 17 operated by electric motor 1019 that powers pump 1017, when tank drive 17 provides sufficient capacity to drive both belt 31 and jet 32. When a hydraulic tank drive 17 does not have sufficient capacity to drive both belt 31 and jet 32, a dedicated electric motor 1019 that drives a dedicated hydraulic pump 317, as shown in FIG. 26 may be used to power only jet 32. Hydraulic pump 317 may be the same as one of hydraulic pumps 1017 shown in FIG. 4 for a system having a dual hydraulic tank drive system. Motor 140 turns shaft 144 which drives impeller 142. In both circumstances, an optional proportional valve 278, also referred to herein as a flow control valve, having an adjusting feature 230 located on console 150 may be used to divert hydraulic fluid that powers motor 140 which in turn powers jet 32. The adjusting device 230 for optional proportional valve 278 may be located on console 150. The shaft of hydraulic motor 140 turns impeller 142 that provides a stream of fluid. Impeller 142 is preferably located within a shroud or enclosure 306 that is in fluid communication with water within the swimming pool, such as through water intake 310. When operating, impeller 142 will draw water from the swimming pool into enclosure 306 through intake 310. Enclosure may include a pipe 305 and impeller 142 may be located at the entrance to pipe 305 or within pipe 305. Impeller 142 propels fluid (water) through pipe 305 which directs the fluid to nozzle 130 in jet 32 through pipe 305. Nozzle 130 is depicted as a converging nozzle, although the nozzle configuration is not so limited. However, a converging nozzle increases the velocity of the exiting fluid. Nozzle 130 in jet 32 may further include an adjustable outlet 312 or 130 that permits the size of the opening to be varied to further increase or decrease the velocity of the exiting fluid. Nozzle 130 may also be adjustable vertically and horizontally to control the direction of the flow of water. A nozzle with an adjustable outlet permits the flow or fluid to be independently controlled by two different means. The proportional valve 278 controls the flow of hydraulic fluid that drives motor 140, thereby controlling the impeller speed. Motor 140 can be driven at a maximum speed, or the flow of hydraulic fluid to motor 140 can be completely shut off to stop the flow of water through jet 32. When water is flowing through nozzle 130, the adjustable outlet feature of nozzle 130 provides a more limited but independent method of adjusting flow by reducing the size of the nozzle opening.

Electric motor 1019 that provides power to drive hydraulic pump 317 or 1019 that powers hydraulic motor 140 are positioned outside of the pool and may be included as part of the non-submergible underwater treadmill portion 12, since such a motor will require an electrical input that may be deemed unsafe. Hydraulic pump 317 may be one of hydraulic pumps 1017 in FIG. 4. FIG. 27 also depicts air inlet 325 connected to pipe 305 to permit air to be injected into jet 32. Air inlet includes an optional in-line valve 1025 that can be opened or closed to permit the injection of air into pipe 305 and hence jet 32. Also, optionally included in the line for air inlet 325 is optional blower motor 1027 that can modulate the amount of air injected into jet 32. As previously set forth, optional functional controls for air inlet 325 and optional blower motor 1027 may be included in console 150.

Figure 10:
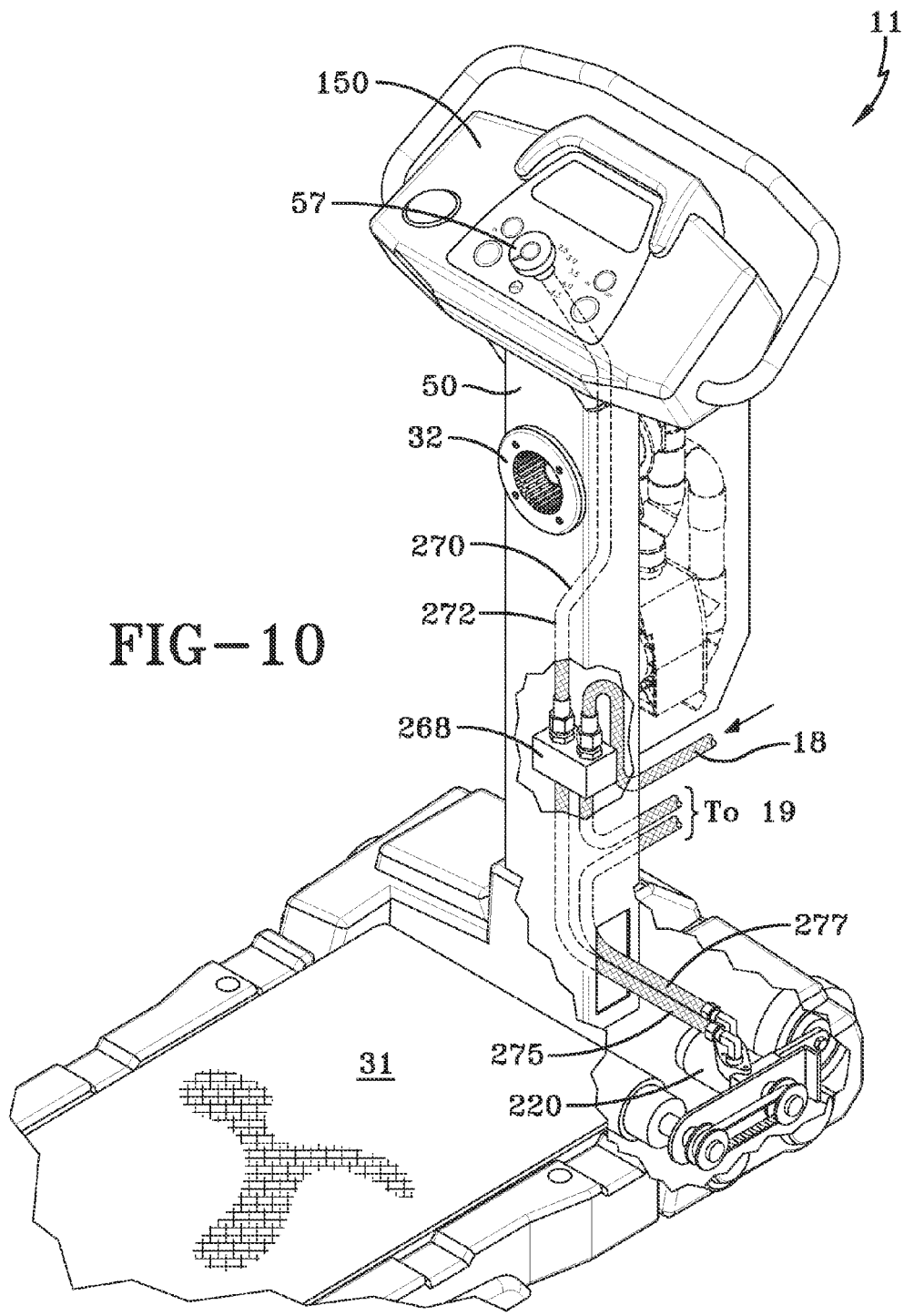
FIG. 10 shows a bottom view of a console of an underwater treadmill system according to an embodiment of the present disclosure.

Referring to FIG. 10, console 150 may be operably connected to the drive motor 220 moving belt 31 and/or a motor 140 (see FIGS. 14 and 26) discharging fluid through jet 32. One or more wires 270 and/or hoses 272 can be operably connected to features within console 150 for monitoring and/or adjusting operation of submergible treadmill portion 11, and one or more wires and/or hoses 350 may be connected for operating or controlling jet 32. Upon adjustment of the control features on console 150, the wires can provide an electrical or electronic signal and/or the hoses may control the hydraulic fluid flow for operating treadmill belt 31. Similar operation is available for jet 32.

Figure 14:
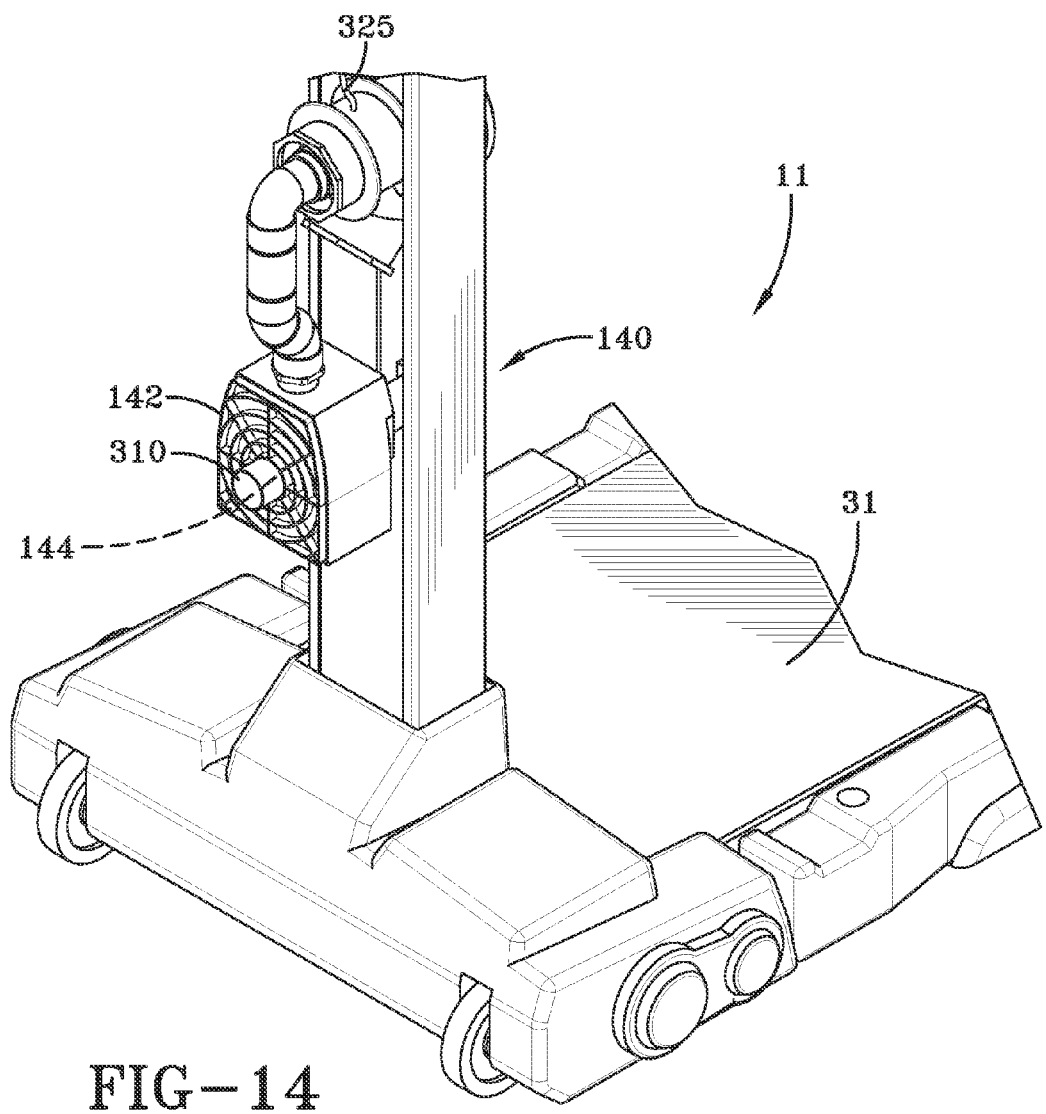
FIG. 14 shows a side view of a portion of an underwater treadmill system according to an embodiment of the present disclosure.
Figure 27:
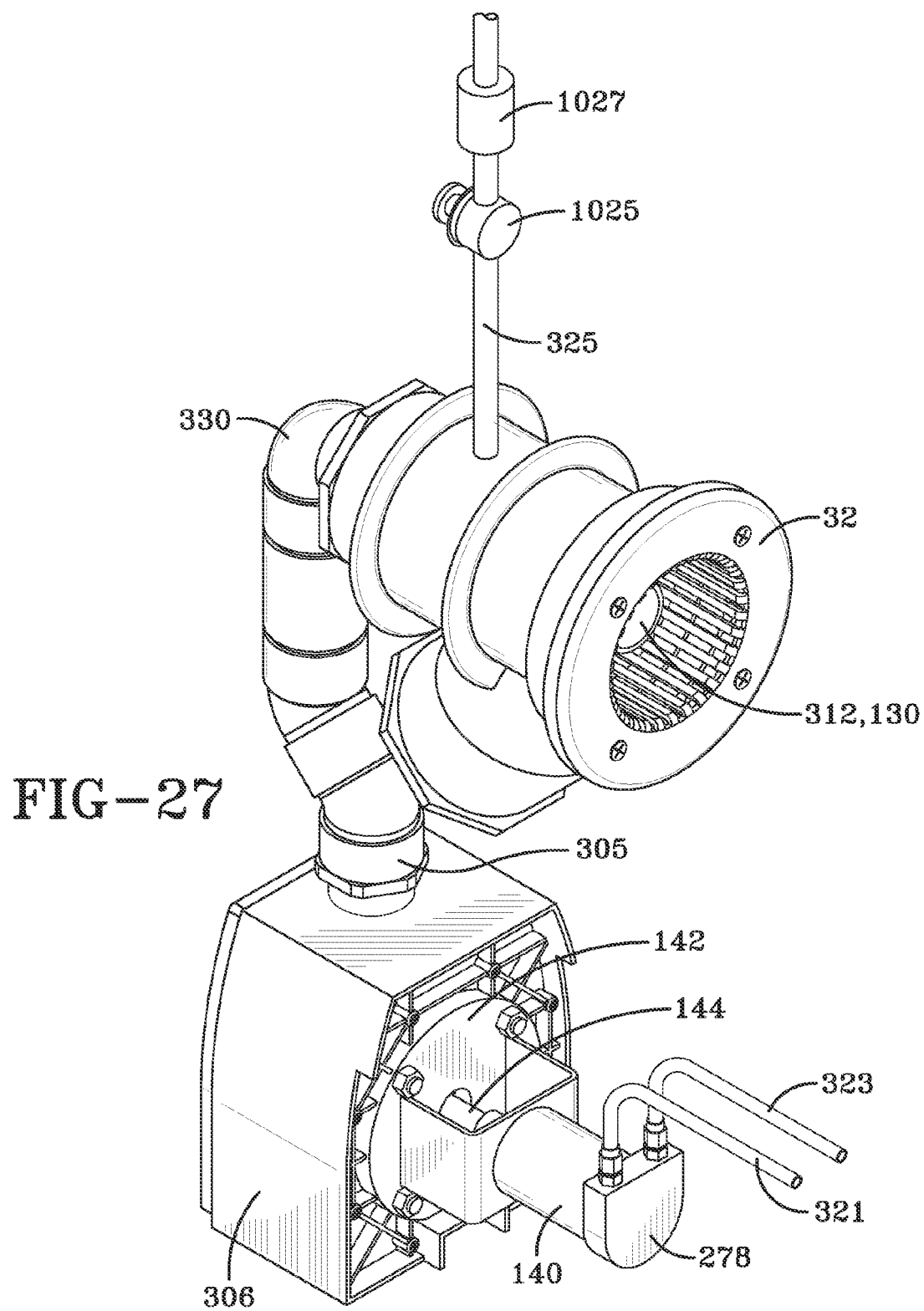
FIG. 27 depicts the arrangement of the hydraulic motor and impeller of FIG. 26 in a preferred embodiment to provide both a stream of fluid that includes both water and air to the jet.

FIGS. 14 and 27 provide one embodiment for the arrangement of the shroud and piping that may operate jet 32, although any other arrangement of piping may be used. As depicted in FIG. 27, penetrations are provided into proportional valve 278 for a hydraulic inlet line 321 and a hydraulic outlet line 323 that provide fluid communication with hydraulic motor 140. Motor 140 includes shaft 144 that turns to rotate impeller 142. However, motor 140 and lines 321 and 323 are part of a system that is sealed from water that may surround it. Impeller 142 is shown in FIG. 27 as adjacent to pipe 305, although impeller may also be within pipe 305. Pipe 305 may include an air inlet 325 that is open to the atmosphere to draw air into the jet stream. Air will naturally be drawn into the jet stream when impeller 142 is in operation. The air inlet thus may include an optional valve 1025 with a control console 150 to permit or completely stop the flow of air into the jet stream. Additionally, an optional blower motor 1027 may be included in air inlet 325 to force additional air into the jet stream, and controls 65 for blower motor 1027 may also be located on console 150.

Figure 28:
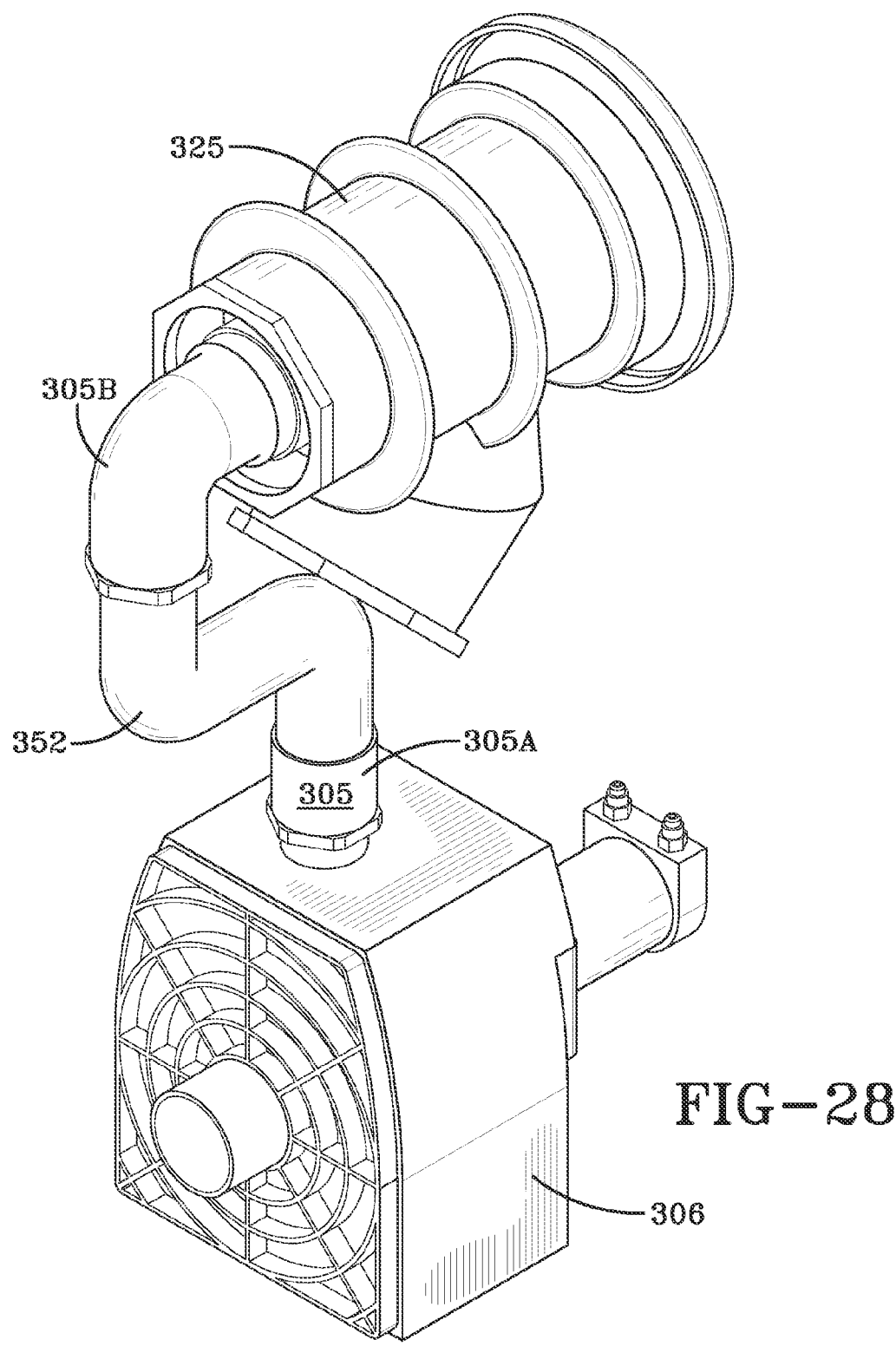
FIG. 28 depicts a preferred embodiment of the impeller arrangement of FIG. 26 using flexible polymer hose to provide water to the jet.

A second preferred embodiment of a piping arrangement is disclosed in FIG. 28. In this arrangement, pipe 305 is a hard plastic pipe that is broken down into two segments, a first segment 305a connected to enclosure or shroud 306 and a second segment 305b that includes jet 32. Second segment 305b may include single turn 330. Second segment 305b also includes a connection for air line 325. Flexible plastic hose 352 extends between first segment 305a and second segment 305b to close the circuit between first segment 305a and second segment 305b to provide a fluid connection enclosure 306 to jet 32. If required, a hose clamp, as shown, may be used to secure flexible hose 352 to either of both first segment 305a and 305b.

Pipe 305 provides the jet stream to nozzle 130 and jet 32, FIGS. 26 and 27. In this embodiment, pipe 305 includes a single turn 330 from the shroud 306 to jet 32 so that all equipment can remain within housing 50. Single turn may vary from about 45° to about 135°, but is preferably about 90°. This arrangement enables a simplified piping arrangement to be placed within or adjacent to housing 50, and reduces friction losses to the jet stream from more complex arrangements that have multiple turns. Ideally, motor 140, impeller 142 and jet 32 are in line with one another, although this arrangement currently increases the size of housing 50.

An electrical or electronic signal can be provided to a controller (not shown) that may control electric features (for example, light(s), start/stop buttons, camera(s), and/or other suitable features) within the submergible treadmill portion 11. In one embodiment, the electrical signal is based upon an electrical input of 12V DC, rated safe, but well-sealed for use in underwater environments.

The treadmill device may be provided with a remote control unit. The remote control unit may be provided to supplement the controls on console 150, or may be provided to completely replace console 150. However, even when a remote control unit completely replaces console 150, a power cut-off switch or kill switch 63 is still provided on the housing. The remote control unit typically includes a transmitter and at least one receiver. The transmitter is operated by the user and it can be used to control any of the controls that are provided on console 150. The receiver receives the signal from the transmitter and controls a feature associated with the treadmill. The remote control transmitter may be battery powered and may transmit a signal in the electromagnetic spectrum, preferably in the infrared frequency, microwave frequency or radio frequency range. The receiver is capable of receiving the signal that causes a response in the treadmill. The receiver may be in communication with a controller that causes the response in the treadmill, or the receiver may directly cause a response. Alternatively, the remote control transmitter may be hardwired to the receiver and may be powered by batteries or may be hardwired to a low voltage DC current. For example, a remote control transmitter may include a buttons that control the operation of the treadmill. One button may control the on/off function and two buttons may control the speed of the belt, one button dedicated to increase the speed and one button to decrease the speed.

Because the preferred embodiment of the treadmill as set forth above includes a treadmill that is hydraulically powered, a servo motor or solenoid may be provided to control proportional valve(s) 268, 278. The servo motor is in communication with the receiver either directly or through a controller. By depressing on button 55, 59, a signal is sent that activates motor 1019 that powers pump 1017, starting movement of the treadmill. To increase or decrease the speed of the belt, the appropriate button is depressed and a signal is received by the receiver, causing the servo motor or solenoid to control the flow through the proportional valve to either increase or decrease the speed of the belt, depending upon which button is selected. To stop treadmill belt 31 or jet 32, off button 56, 58 is depressed again, and a signal is sent that deactivates motor 1099. In a like fashion, additional buttons can be added to control other features of the treadmill. For example, buttons can be included on the remote control to control jet 32 in a similar fashion as well as an optional blower motor 1027. Lights and a camera may be provided with the treadmill and buttons can be included on the remote transmitter to control the operation of features associated with this equipment. The remote control may also include buttons to control images displayed on display window 232. A video monitor or other monitoring device also may be added, and buttons can be included on the remote to control the operation of the monitoring device, allowing it to display, for example, television shows, DVDs, output from the treadmill camera, information related to treadmill speed, treadmill inclination, water temperature, jet flow rate, heart rate/pulse rate etc. Depending on the features that are desired to be controlled by the remote control unit, it may be necessary to provide additional servo motors in communication with the receiver or the controller, as described above, for control of the proportional valve(s) 268, 278, and thus the speed of belt 31 or operation of jet 32.

Figure 12:
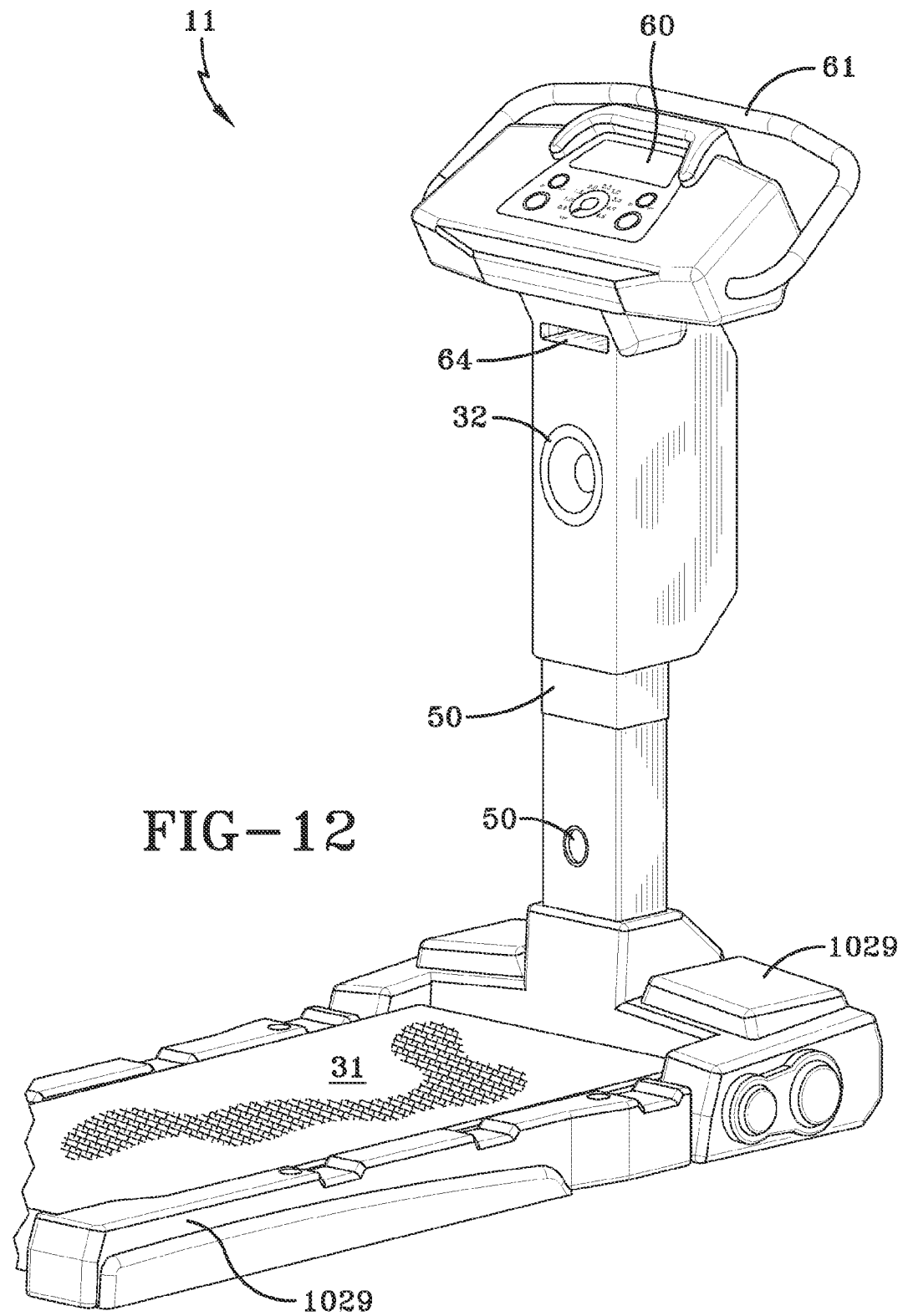
FIG. 12 shows a perspective view of a portion of an underwater treadmill system according to an embodiment of the present disclosure.

In the embodiment shown in FIG. 12, the electrical or electronic signal can control/adjust a camera 51. In the embodiment shown in FIG. 12, the electronic signal can control/adjust a video monitor that is visible in display window 232 or display input from other suitable media interface, such as a camera 51, while providing controls for a light 62. Display window 232, camera 51, and/or lights 62 can be operated by controls in console 150 or by a remote control, as discussed above. Video monitor 60, camera 51, and/or lights 62 can be operated in conjunction with external electronics (not shown) for displaying images (still or video) from the camera, for controlling the intensity and/or color of light 62, and/or a computer (not shown) for providing information to display window 232 (for example, information about the progress of the routine, a computer to provide automated adjustments to workout routines, heart/pulse rate monitor, a computer to provide automated adjustments to routines based on real-time heart rate monitoring, visual messages from a trainer, or other suitable information). These functions can be provided by integrated circuit or a controller positioned within housing 50 or console 150. The treadmill also conveniently may provide IPOD connectivity.

Camera 51 is an important auxiliary feature for rehabilitation. Camera 51 allows for real-time analysis of gait of the user, which can provide an indication of how the body is recovering from an injury or how it is responding to therapy. The user can assess this by connecting the camera 51 to a video screen that is ideally within view of the user. Camera 51 may also be connected to a remotely located medical professional who is thereby provided with the capability of real-time monitoring of the patient's activity. Alternatively, the output of camera 51 may be connected to a recording device so that a medical professional or therapist can review the results of one or more sessions to assess progress or lack thereof. Lighting 62 is provided not solely for ambiance, but to provide sufficient illumination so that the camera 51 can perform its function. While camera 51 is shown located in the console, camera 51 may be located anywhere along the perimeter of the treadmill by providing a camera housing (not shown) along the perimeter 1029 and providing power to camera 51, if required. One or more cameras 51 may be used, so that multiple views can be provided. These multiple views can be displayed selectively or simultaneously on a screen or multiple screens and, of course, the images from each camera 51 can be individually recorded.

Figure 13:
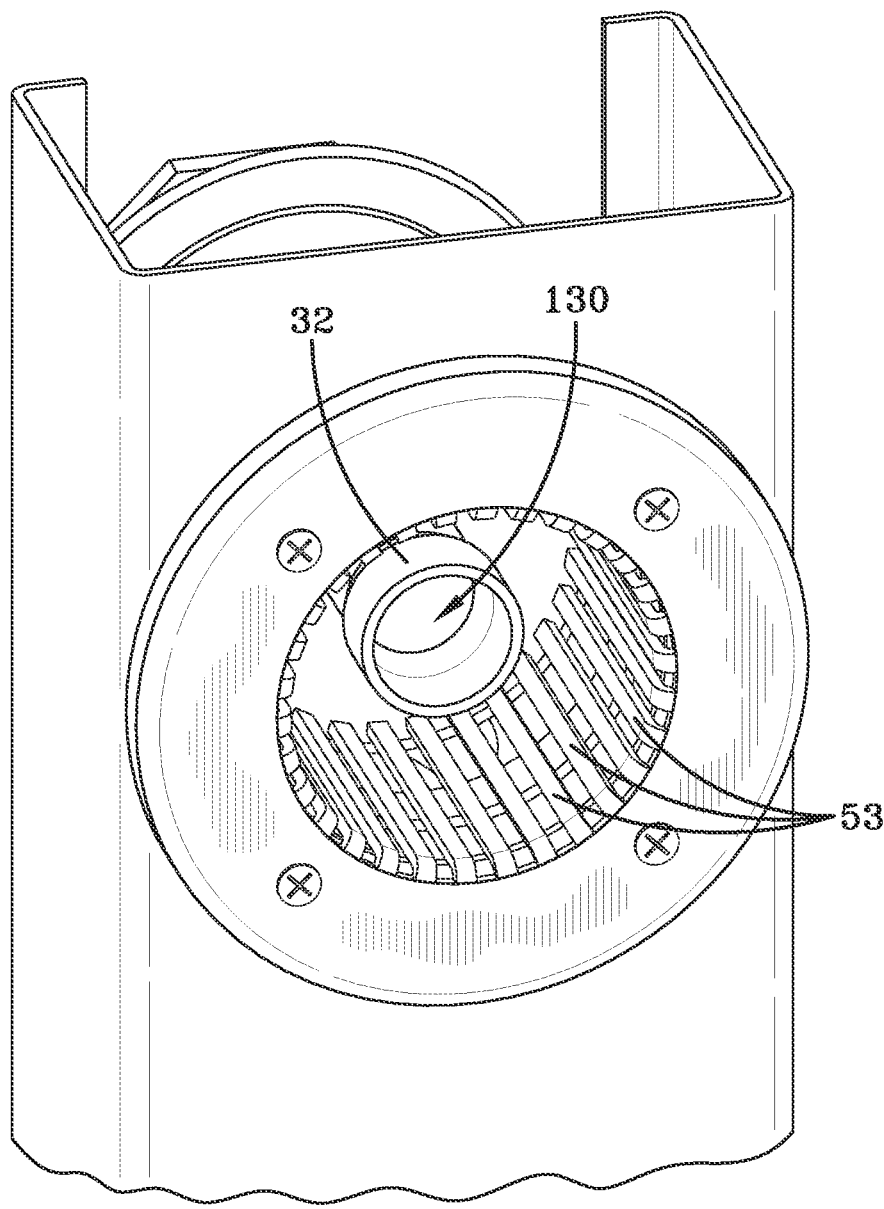
FIG. 13 shows a perspective view of a portion of an underwater treadmill system according to an embodiment of the present disclosure.

FIG. 13 shows an exemplary embodiment of a portion of the submergible treadmill portion 11. In this embodiment, jet start mechanism 58, and/or the jet stop mechanism 59, FIG. 9, respectively activate or deactivate jet 32, which further includes a manual adjustment feature of nozzle 130. Through manual adjustment, the nozzle feature 130 permits the jet 32 to be adjusted by rotation through 360° to direct the flow of water in a selected direction. Adjustment of jet 32 can permit the user to direct the jet for a back massage, to target a specific area of the user's body for a massage and to direct water and/or air up or down on the user's body. Nozzle 130 can also be turned so that the velocity of the water and/or air, can be increased or decreased by rotating nozzle into or out of a plane perpendicular to the flow of water. It can also be adjusted to increase and/or decrease an area of the body contacted by the water and/or air from the jet 32 which controls the velocity of the flow of the jet stream. Additionally or alternatively, adjustment of jet 32 can be configured for automatically and/or manually increasing and/or decreasing resistance based upon water level, buoyancy, body weight, wheel levels, positioning with pool 15, and/or other suitable factors. In one embodiment jet 32 and/or nozzle 130 can be adjusted based upon water level, body position, or through software-executed algorithms incorporating one or more of these parameters or other suitable parameters. For example, adjustment of adjustment feature 130 can increase flow (open) or decrease flow (partially closed position) based upon a signal (electronic or mechanical) provided in conjunction with the software-executed algorithm based on automated work-out routines. Nozzle 130 can be automatically adjusted to increase the force delivered by jet 32 as the treadmill speed increases, or alternatively, to decrease the force delivered by jet 32 as treadmill speed increases. Nozzle 130 can be configured to receive predetermined replaceable types of nozzles (for example, a massaging spray head). In addition to providing a massage, jet 32 can be used to increase the resistance experienced by a user during a workout to simulate a current so that a user can perform other activities such as swimming, as previously discussed. Hoses 321, 323 providing hydraulic fluid to motor 140 can be provided with quick connect/disconnect fittings. Return grating 53 provides an unobstructed flow path for water to flow to the interior of housing 50.

Figure 15:
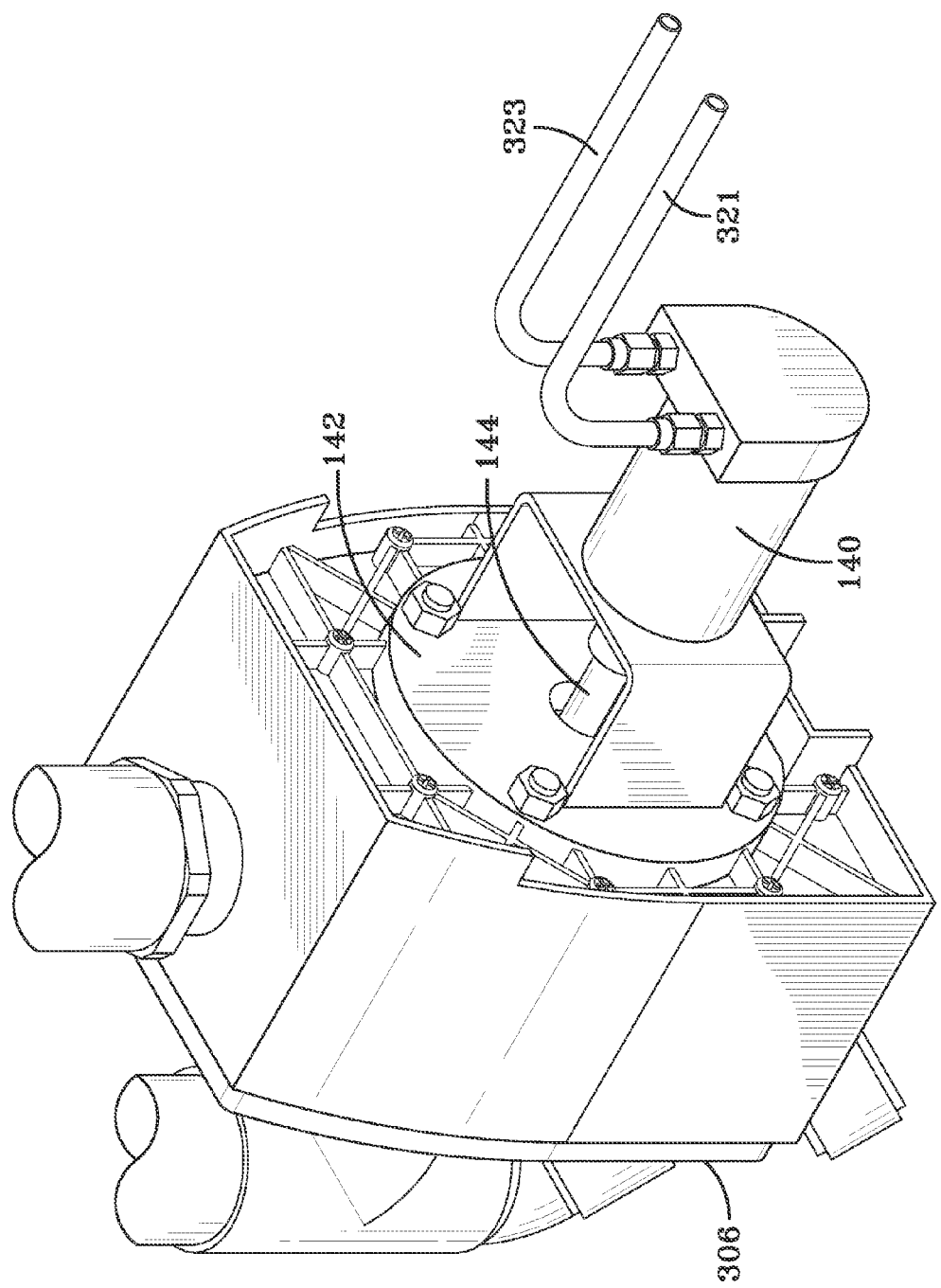
FIG. 15 shows a perspective view of a motor of an underwater treadmill system according to an embodiment of the present disclosure.
Figure 16:
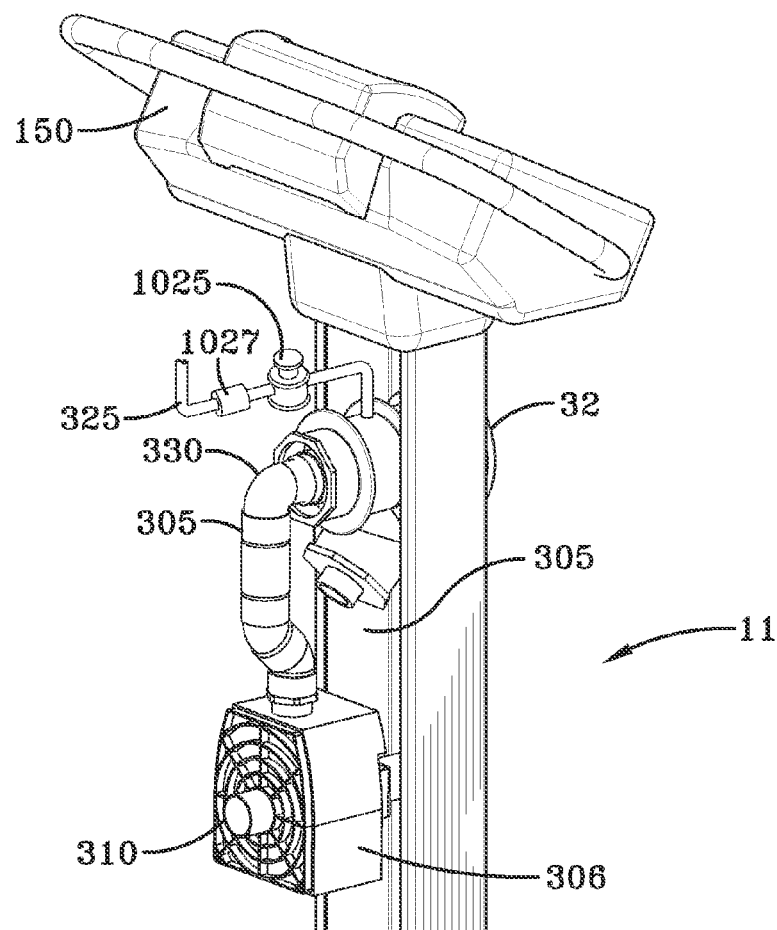
FIG. 16 shows a perspective view of a portion of an underwater treadmill system collapsed and tilted for repositioning according to an embodiment of the present disclosure.

FIGS. 14-16 show one embodiment of a hydraulic motor 140 for driving jet 32. Motor 140 is driven by hydraulic fluid from pump 1017 from the non-submergible portion 12. Motor 140 drives air and/or water through the jet 32. The air and/or water received by the motor 140 can be provided from any suitable source. Hydraulic fluid from pump 1017 is provided by a hose 321 and is returned to pump 1017 through a hose 323. In one embodiment, motor 140 drives impeller 142 connected to shaft 144 at a constant speed. The impeller draws water from intake 310 and a separate air inlet 325 injects air (to increase resistance) into the water to form a stream that is expelled from the jet 32. Air may be drawn into jet 32 from a small tube or pipe that is integral with the housing, extending above the water level that may include a small blower motor 1027. Jet 32 includes at least one water intake 310.

Referring again to FIGS. 14 and 15, in one embodiment, water is drawn into at least one intake 310 by impeller 142 and expelled by jet 32. This configuration permits intake 310 to be positioned close to the impeller 142, thereby permitting a low amount of force to draw water into the intake 310. The velocity and/or amount of air and/or water being expelled from jet 32 (or drawn into the intake 310) may be selectively adjusted based upon the configuration of console 150 and/or the nozzle 130 of jet 32 and/or intakes 310. In one embodiment, water may be drawn by one or more inlets. In one embodiment, air may be drawn from outside of the pool 15 (i.e. the atmosphere above the water surface) and water may be drawn from within pool 15 and through the at least one intake 310. In this embodiment, both water and air may be expelled from jet 32 by having a connection that selectively allows any available pool jets to be connected to integrated jet 32. In one embodiment, pool jets may be used to augment the force of water and/or air coming through jet 32. In one embodiment, jet 32 can be substantially devoid of water and/or air from pool jets, thereby allowing the submergible underwater treadmill portion 11 to be portable (able to be moved to different pools) and/or positionable (able to be moved to different portions of the pool 15). Referring to FIG. 16, in one embodiment, submergible treadmill portion 11 can be collapsed, tilted, and rolled on one or more wheels 260 to a different portion of pool 15, along the deck 14 to be stored, stored within pool 15.

Figure 11:
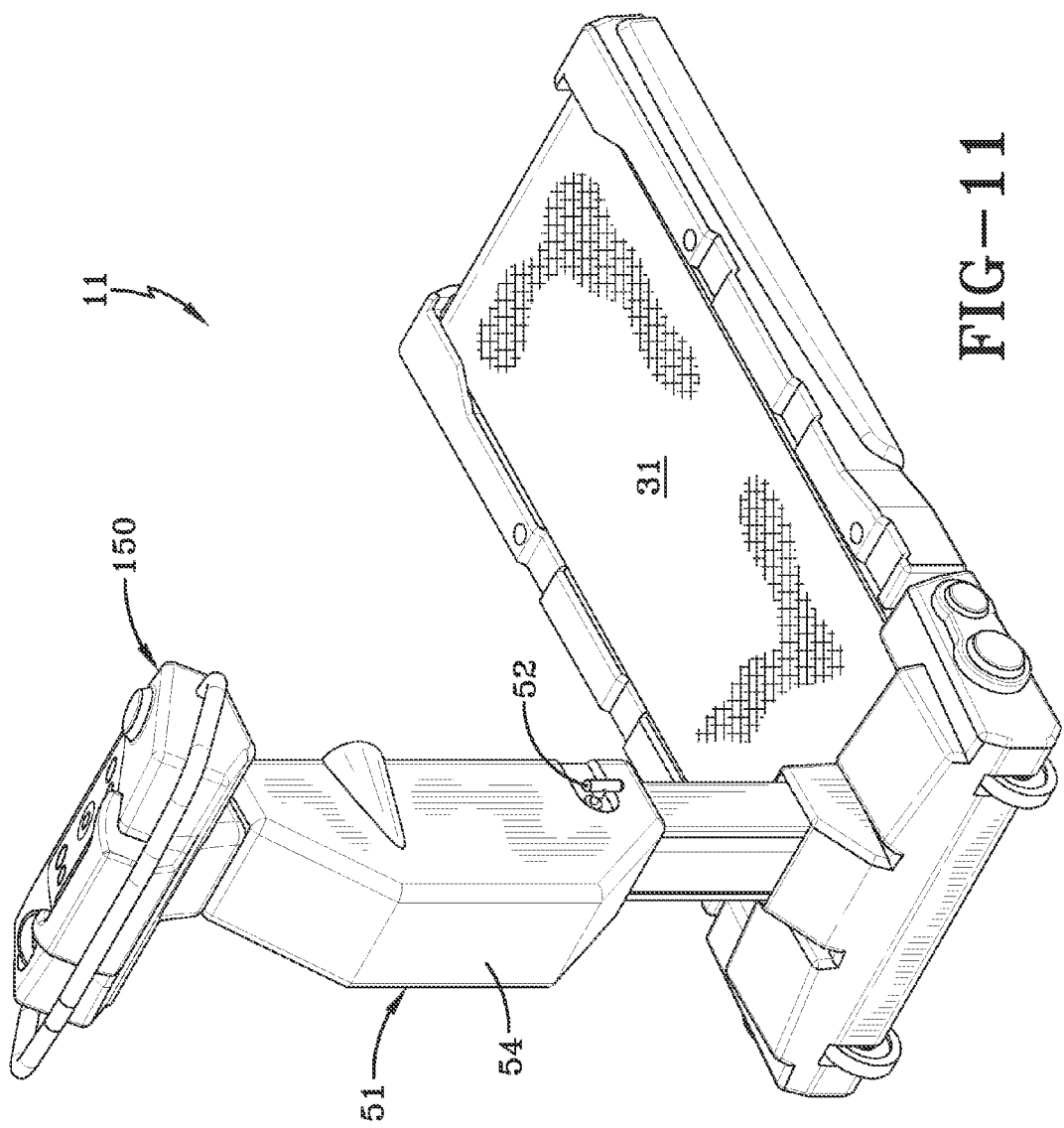
FIG. 11 shows of a perspective view of a portion of an underwater treadmill system according to an embodiment of the present disclosure.
Figure 17:
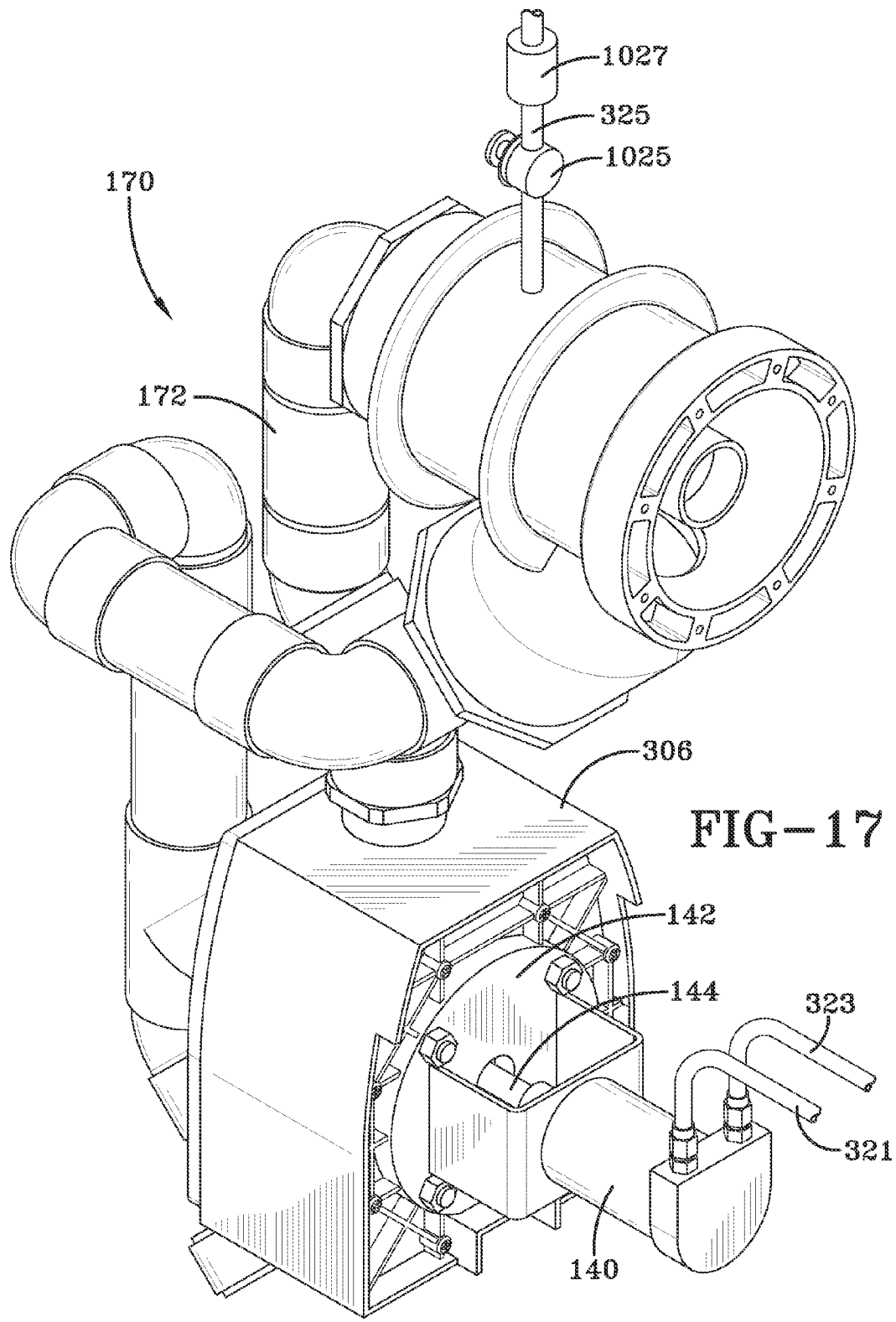
FIG. 17 shows a perspective view of plumbing of an underwater treadmill system according to an embodiment of the present disclosure.
Figure 18:
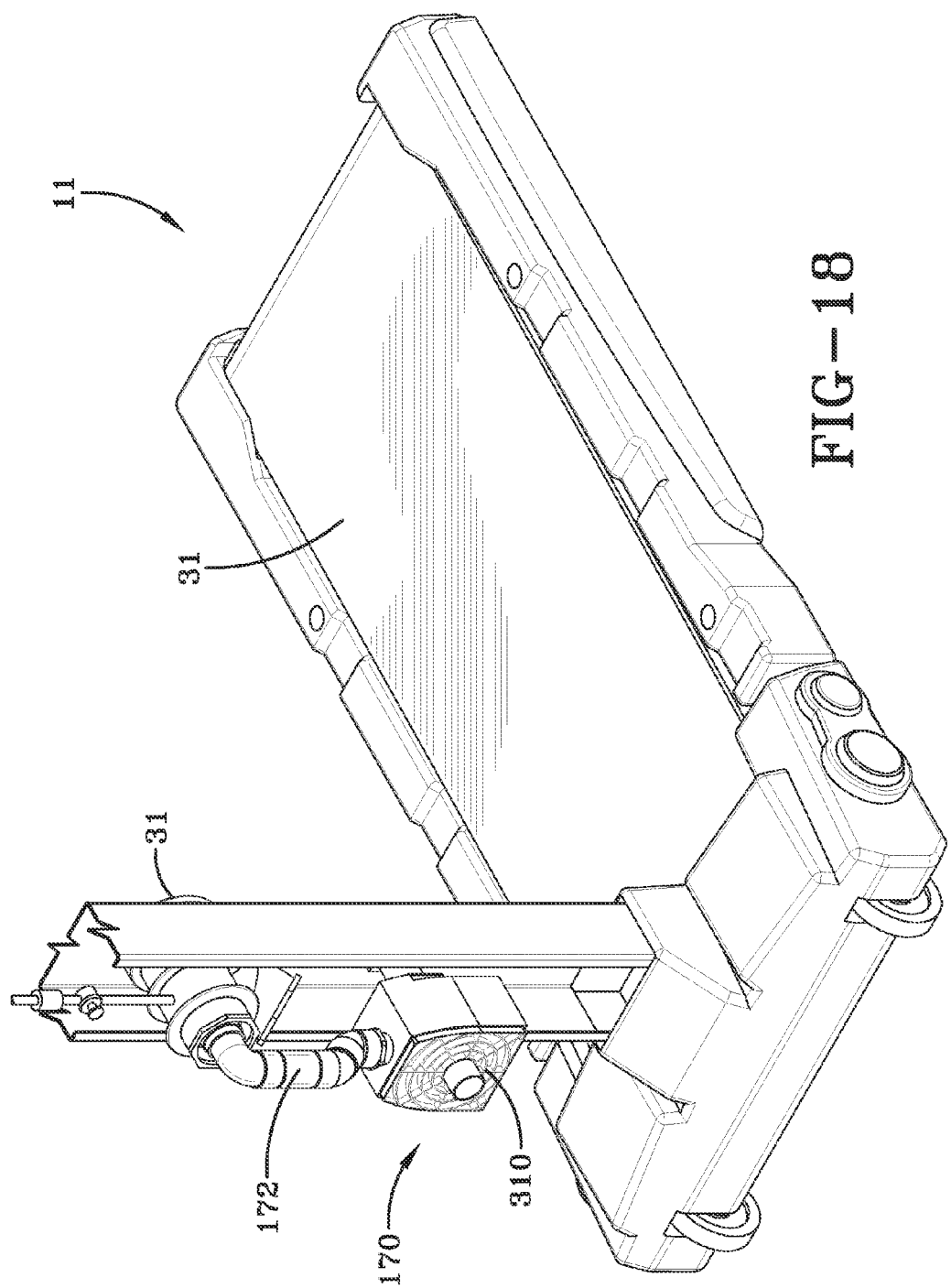
FIG. 18 shows a perspective view of a portion of an underwater treadmill system according to an embodiment of the present disclosure.
Figure 19:
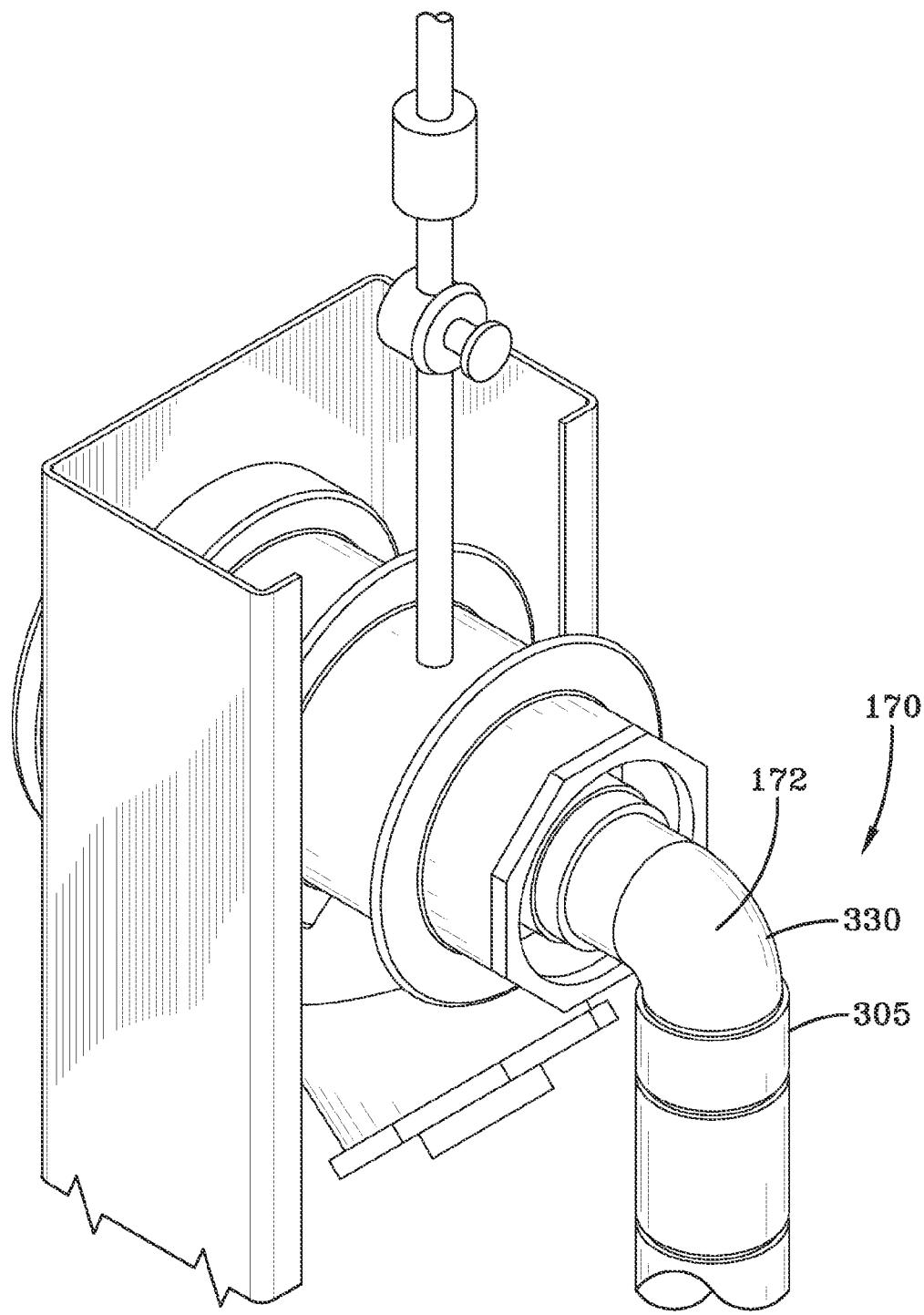
FIG. 19 shows a perspective view of plumbing of an underwater treadmill system according to an embodiment of the present disclosure.

Referring again to FIG. 11, in one embodiment, submergible underwater treadmill portion 11 includes a securing feature 52 for selectively releasing a cover 54 from housing 50, thereby exposing plumbing 170 (see FIG. 17). Referring to FIGS. 17, 18, and 19, the submergible treadmill portion 11 includes plumbing 170 for supply air and/or water to jet 32 and hydraulic fluid to motor 140 that drives jet 32. Jet adjustments are accessible on removal of cover 54. Flow of water and/or air can be controlled by controlling the flow of fluids through plumbing 170 by adjustments to plumbing when controls are not provided on console 150. Similarly, when the configuration is set for low velocity and/or amount of air and/or water, the plumbing 170 within the submergible treadmill portion 11 can be configured to increase an amount of air and/or water being recycled back to enclosure 306 through return supply conduit 172, thereby decreasing the velocity and/or amount of water and/or air being expelled by jet 32 and reducing flow volume.

Figure 20:
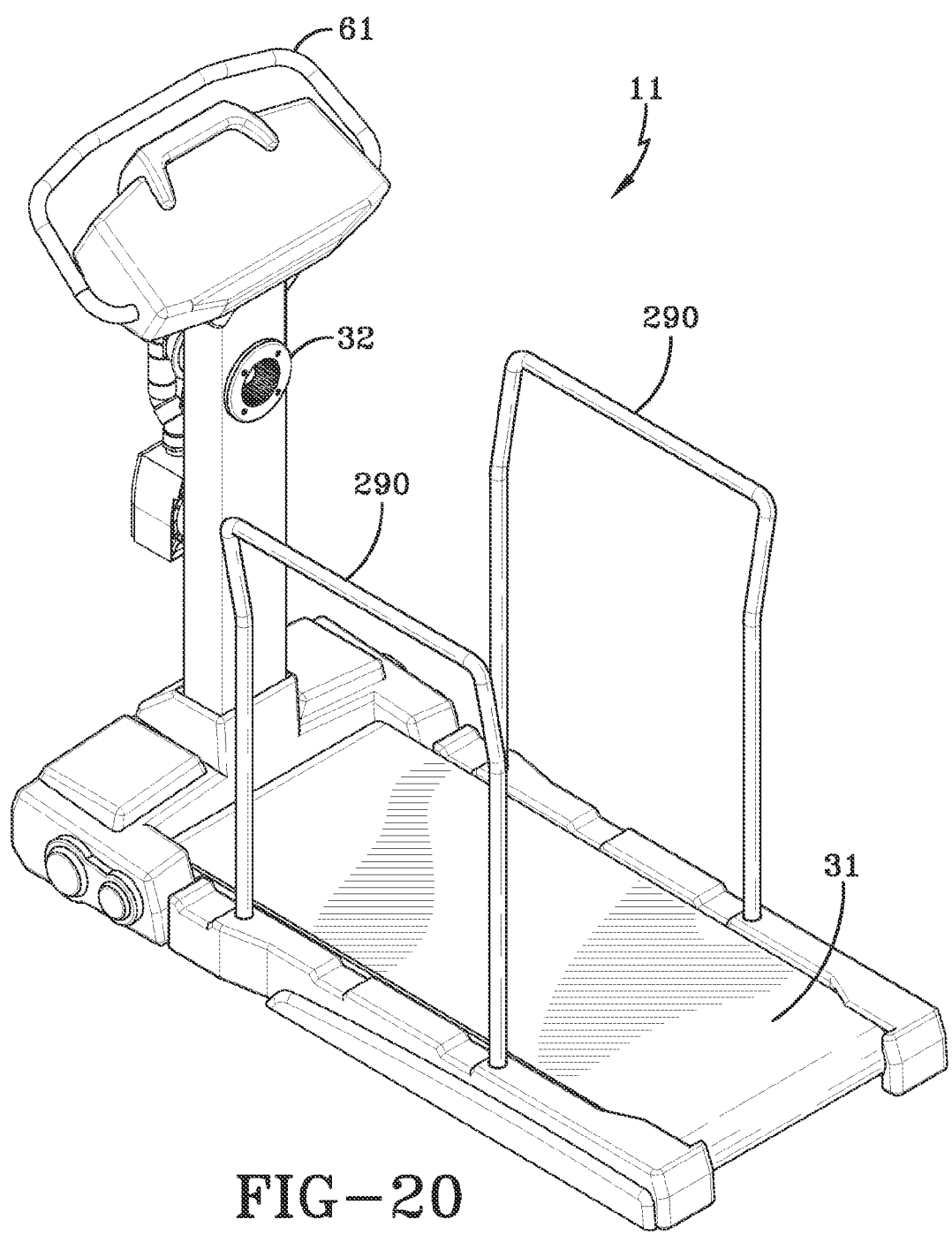
FIG. 20 shows a perspective view of a portion of an underwater treadmill system having treadmill rails according to an embodiment of the present disclosure.
Figure 21:
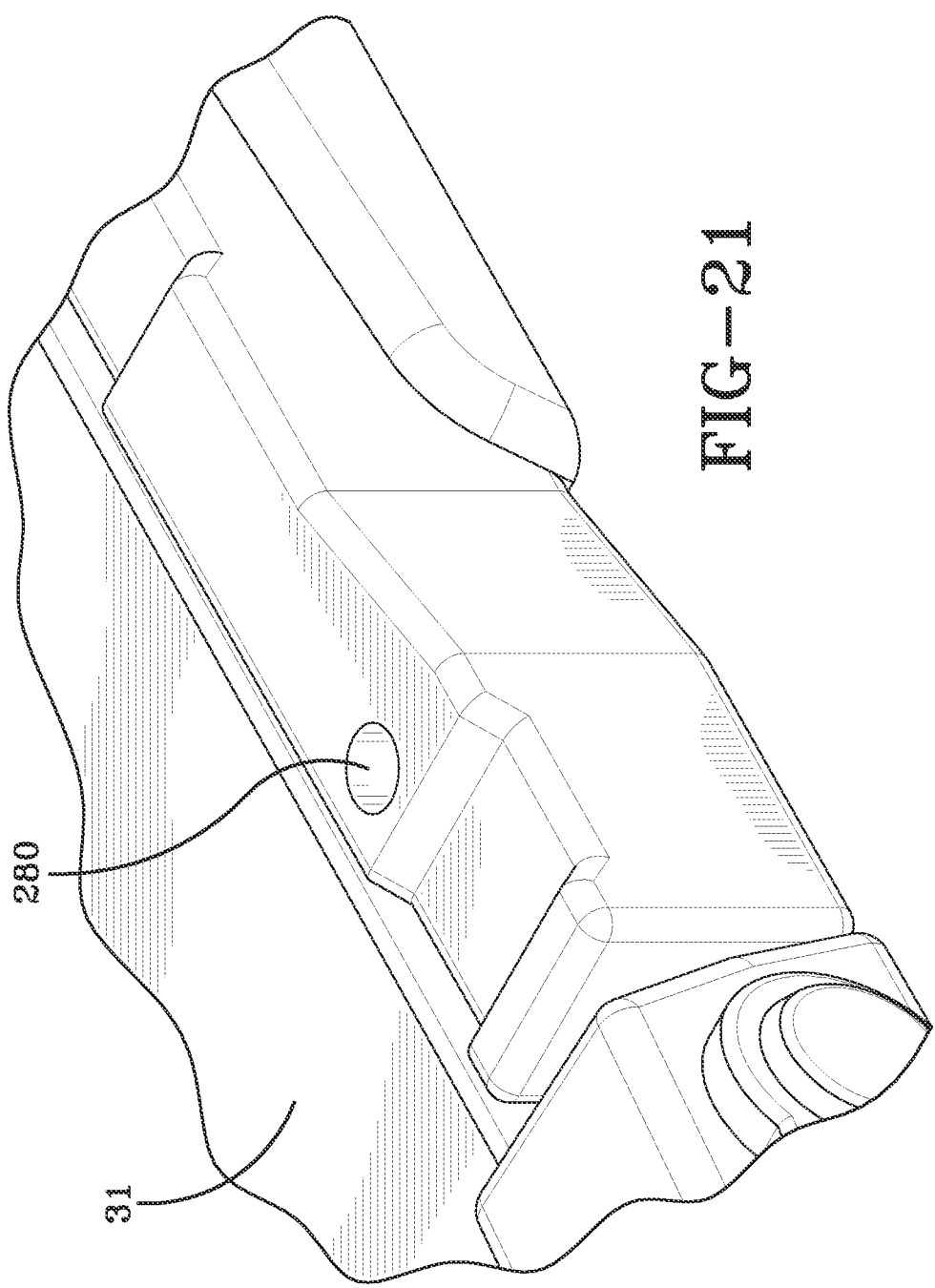
FIG. 21 shows a perspective view of a portion of an underwater treadmill system having features for engaging treadmill rails according to an embodiment of the present disclosure.

Referring again to FIG. 12, submergible underwater treadmill portion 11 can include a fixed handrail 61 mounted to housing 50. Fixed handrail 61 is also used for lifting submerged, underwater treadmill portion 11. Referring to FIG. 20, the submergible underwater treadmill portion 11 can also include one or more removable treadmill rails 290 positioned parallel to the belt 31. Handrail 61 and/or the treadmill rails 290 can be used for maintaining balance on high resistance exercise routines, facilitating additional exercise capabilities, and/or facilitating massages. Treadmill rail(s) 290 can be positioned within apertures 300 (see FIG. 21) or recesses sized and shaped to receive the treadmill rail(s) 290. Apertures 280 and/or the treadmill rail(s) 290 can include locking features (for example, slots) permitting the treadmill rail(s) 290 to be temporarily secured. The treadmill rail(s) 290 can include features permitting adjustment of height and or length such as telescoping tubes. In one embodiment, the treadmill rail(s) 290 are adjustable permitting the handrail to be used as a side rail (see FIG. 20) and/or a cross rail 300 (see FIG. 22).

Prior art treadmills utilize a tensioning device that includes a screw mechanism positioned longitudinally along each side of the treadmill. These screw mechanisms require frequent adjustment and tend not be reliable. The adjustment mechanism of the present invention provides a positive tensioning mechanism. The adjustment mechanism provides a pair of telescoping tubes, a first tube 702 within a second tube 704, the tubes being movable with respect to one another between the tubes as shown in FIG. 23A-D and FIG. 24A-D. At the end of the tubes are a pair of nuts 706, 708. One pair of telescoping tubes extends longitudinally along each side of the treadmill frame, a bracket 710 such as shown in FIG. 23B being bolted to the frame, see FIG. 1 or FIG. 5. To adjust the length of either side of the frame, first nut 708 is loosened and tubes are adjusted by turning second nut 706 which increases or decreases the overall length of the mechanism as one tube moves with respect to the other. The tubes, 702, 704 move with respect to one another to lengthen or shorten the frame until the proper length is provided on each side that centers the tread on the frame with the proper tension is attained. Nut 708 is tightened against nut 706 preventing any further movement of tubes 702, 704 with respect to each other and providing a positive locking mechanism that inhibits further movement of the belt as a result of shifts in the frame. As the belt ages and elongates, additional adjustments may be required.

Although the underwater treadmill having an integrated jet device has been described with regard to a hydraulically driven treadmill, this is only a preferred embodiment, and the treadmill may be driven by any suitable driving system. For example, the treadmill may be driven by an electrical power source, provided that such an electrical power source can deliver sufficient power and can be properly grounded so that it provides no electrical hazards to the user.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. An underwater treadmill system, comprising:
    a treadmill belt portion, the treadmill belt portion including a continuous belt extending around a drive roller at a first end and an idler roller at a second end;
    a housing connected to the treadmill belt portion;
    a mechanism for moving the treadmill belt portion and housing from a first location to a second location within a pool;
    a power source to drive the treadmill belt;
    wherein the housing includes a jet, a direction of a stream emanating from the jet being adjustable in a direction toward a surface of water, in a direction toward a surface of the treadmill belt portion and included angles there between; and
    wherein the treadmill belt portion is movable from a first operational position substantially perpendicular to the housing to a second storage position substantially parallel to the housing.

2. The system of claim 1, wherein water flow from the jet is selectively adjustable.

3. The system of claim 2, wherein water flow is adjustable to provide a current having a sufficient force to permit a swimming activity by a user.

4. The system of claim 1, wherein the jet is capable of selectively adjusting water flow in conjunction with the adjustment of the treadmill belt portion.

5. The system of claim 1, further comprising a cover configured to fit over the system when the treadmill belt portion is in the second storage position substantially parallel to the housing.

6. An underwater treadmill system, comprising:
a treadmill belt portion, the treadmill belt portion including a continuous belt extending around a drive roller at a first end and an idler roller at a second end;
a housing connected to the treadmill belt portion;
a mechanism for moving the treadmill belt portion and housing from a first location to a second location within a pool;
a power source to drive the treadmill belt;
wherein the housing includes a jet, a direction of a stream emanating from the jet being adjustable in a direction toward a surface of water, in a direction toward a surface of the treadmill belt portion and included angles there between; and
wherein the system further includes a camera configured to capture an underwater image.

7. The system of claim 6, wherein the system further includes a light to provide underwater illumination.

8. An underwater treadmill system, comprising:
a submergible treadmill portion having a fluid-driven treadmill belt, the treadmill belt including a continuous belt extending around a drive roller at a first end and an idler roller at a second end;
a power source to drive the fluid-driven treadmill belt, the power source being a first hydraulic pump providing a fluid at a constant speed; and
a housing connected to the treadmill portion, the housing including a console;
wherein the housing includes a jet having a nozzle, a direction of a stream of water emanating from the jet nozzle being adjustable in a direction toward a surface of water, in a direction toward a surface of the treadmill belt and included angles there between; and
a proportional valve, wherein velocity of the treadmill belt is changed by adjusting the flow of fluid from the first hydraulic pump powering the treadmill belt using the proportional valve.

9. The system of claim 8 wherein the fluid-driven treadmill belt is powered by a first hydraulic motor powered by fluid from the first hydraulic pump that is driven by a single speed alternating current motor in the power range of 1-3 horsepower.

10. The system of claim 9 wherein the first hydraulic motor is driven by the first hydraulic pump, the system further including a proportional valve to adjust an amount of fluid flowing to the first hydraulic motor from the first hydraulic pump, the proportional valve being controlled from the housing.

11. The system of claim 9 wherein the jet is powered by a second hydraulic motor driven by a second hydraulic pump, the system further including a flow control valve to adjust the fluid flowing to the second hydraulic motor from the second hydraulic pump, the flow control valve being controlled from the housing.

12. The system of claim 8 wherein the jet nozzle produces the stream of water, the nozzle powered by an impeller that that is driven by a hydraulic motor.

13. The system of claim 12 further including a conduit, the conduit in fluid communication with the jet nozzle, the conduit extending toward the motor from the housing.

14. The system of claim 13 wherein the conduit includes a single bend of from about 45° to about 135° so that the conduit, hydraulic motor and impeller can provide a flow of water to the jet nozzle, and the conduit, nozzle and hydraulic motor can be positioned within the housing.

15. The system of claim 8 further including means for adding air to the stream of water.

16. The system of claim 15 wherein the means for adding air to the stream of water further includes a blower, the blower being controlled from the housing.

17. An underwater treadmill system, comprising:
a submergible treadmill portion, the treadmill portion including a continuous belt extending around a drive roller at a first end and an idler roller at a second end;
a housing connected to the submergible treadmill portion;
a jet within the housing emanating a stream of water;
a power source to drive the continuous belt of the treadmill portion and the jet;
wherein a direction of the stream emanating from the jet is adjustable in a direction toward a surface of water, in a direction toward a surface of the treadmill belt and included angles there between; and
wherein a first power source drives the treadmill belt and a second power source drives the jet.

18. The underwater treadmill of claim 17 wherein the first power source driving the belt is selected from the group consisting of a hydraulic drive motor, low voltage DC current and self-propulsion by a user.

19. The underwater treadmill of claim 17 wherein the second power source is a selected from the group consisting of low voltage DC current and hydraulic fluid.

20. The underwater treadmill of claim 19 wherein the second power source is driven by a low voltage DC current.

21. The underwater treadmill of claim 19 wherein the second power source drives a blower motor.

22. The underwater treadmill of claim 17 further including a mechanism for moving the treadmill portion and housing from a first location to a second location within a pool.

23. The underwater treadmill system of claim 22 wherein the mechanism for moving the treadmill portion and housing from a first location to a second location includes one or more wheels.

* * * * *